United States Patent
Taguchi et al.

(10) Patent No.: US 9,532,759 B2
(45) Date of Patent: Jan. 3, 2017

(54) X-RAY CT APPARATUS, IMAGE PROCESSING APPARATUS, AND IMAGE PROCESSING METHOD

(71) Applicant: TOSHIBA MEDICAL SYSTEMS CORPORATION, Otawara-Shi (JP)

(72) Inventors: Hiroki Taguchi, Otawara (JP); Tatsuo Maeda, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 14/326,889

(22) Filed: Jul. 9, 2014

(65) Prior Publication Data
US 2014/0321603 A1 Oct. 30, 2014

Related U.S. Application Data

(63) Continuation of application No. PCT/JP2013/073405, filed on Aug. 30, 2013.

(30) Foreign Application Priority Data

Aug. 30, 2012 (JP) ................... 2012-189917
Aug. 30, 2013 (JP) ................... 2013-179627

(51) Int. Cl.
*A61B 6/03* (2006.01)
*A61B 6/00* (2006.01)
*H05G 1/32* (2006.01)

(52) U.S. Cl.
CPC .............. *A61B 6/482* (2013.01); *A61B 6/032* (2013.01); *A61B 6/405* (2013.01); *A61B 6/481* (2013.01);

(Continued)

(58) Field of Classification Search
CPC ......... A61B 6/032; A61B 6/405; A61B 6/481; A61B 6/482; A61B 6/5217; A61B 6/54; A61B 6/4035; A61B 6/502; A61B 6/583; A61B 6/025; A61B 6/06; A61B 6/4021; A61B 6/4028; A61B 6/4233; A61B 6/4241; A61B 6/4266; A61B 6/4291; A61B 6/4411; A61B 6/463; H01G 1/32; A61N 7/02; A61N 2005/1054; A61N 2005/1061; H04N 1/4097; H04N 1/58; G01V 5/00008; G01V 5/0025; G01T 1/161; G06T 5/50; G06T 11/00; G06T 11/60; G06T 2207/10008; G06T 2207/10024; G06T 2207/10048; G06T 2207/10116

(Continued)

(56) References Cited

U.S. PATENT DOCUMENTS 8,761,479 B2 * 6/2014 Avinash ................. A61B 6/032
  382/131
2009/0147919 A1 6/2009 Goto et al.

(Continued)

FOREIGN PATENT DOCUMENTS

CN 1518955 A 8/2004
CN 102462504 A 5/2012

(Continued)

OTHER PUBLICATIONS

International Search Report mailed Oct. 1, 2013 for PCT/JP2013/073405 filed Aug. 30, 2013 with English Translation.

(Continued)

*Primary Examiner* — Glen Kao
*Assistant Examiner* — Chih-Cheng Kao
(74) *Attorney, Agent, or Firm* — Oblon, McClelland, Maier & Neustadt, L.L.P.

(57) ABSTRACT

An X-ray CT apparatus includes an image generating unit, a discrimination unit, a monochromatic X-ray image generating unit, a combined-image generating unit and a display unit. The image generating unit generates a plurality of reference material images corresponding to respective ones of a plurality of reference materials on a basis of pre-reconstruction data of multi-energy obtained by scanning a subject. The discrimination unit discriminates each of a plurality of materials contained in an imaging region of the subject on a basis of the plurality of reference material images. The monochromatic X-ray image generating unit generates a monochromatic X-ray image at energy determined by each of the plurality of discriminated materials. The combined-image generating unit combines a plurality of monochromatic X-ray images corresponding to the plurality of materials and to generate a combined image. The display unit displays the combined image on a display device.

15 Claims, 14 Drawing Sheets

(52) U.S. Cl.
CPC ............... *A61B 6/5217* (2013.01); *A61B 6/54* (2013.01); *H05G 1/32* (2013.01)

(58) Field of Classification Search
USPC .............................................. 378/4, 9, 5, 62
See application file for complete search history.

(56) References Cited

U.S. PATENT DOCUMENTS

2010/0303196 A1    12/2010  Zou
2013/0142412 A1*  6/2013  Oh ....................... A61B 6/4241
                                                                    382/132

FOREIGN PATENT DOCUMENTS

| JP | 2006-320464 A | 11/2006 |
| --- | --- | --- |
| JP | 2009-261942 A | 11/2009 |
| JP | 2010-274108 A | 12/2010 |
| JP | 2011-110245 A | 6/2011 |
| JP | 2011-136002 A | 7/2011 |
| JP | 2011-172803 A | 9/2011 |
| JP | 2011-244875 A | 12/2011 |
| JP | 2012-081108 A | 4/2012 |

OTHER PUBLICATIONS

Johnson TR. et al., "Material differentiation by dual energy CT: initial experience", Eur Radiol (2007), 17, 1510-1517. Abstract only of this dissertation is attached.
English translation of the International Preliminary Report on Patentability and Written Opinion issued Mar. 3, 2015 in PCT/JP2013/073405.
Combined Chinese Office Action and Search Report issued Jan. 14, 2016 in Patent Application No. 201380008634.5 (with Japanese translation and English translation of categories of cited documents).

* cited by examiner

| MATERIALS | ENERGY |
|---|---|
| A | 75keV |
| B | 60keV |
| C | 60keV |
| ⋮ | ⋮ |
| BONE | 130keV |
| ARTIFACT | 130keV |

ENERGY TABLE

FIG. 7

| MATERIALS | ENERGY |
|---|---|
| SOFT TISSUE 1 | 80keV |
| SOFT TISSUE 2 | 50keV |
| SOFT TISSUE 3 | 50keV |
| BONE | 130keV |
| ARTIFACT | 130keV |

FIG. 9

X-RAY CT APPARATUS, IMAGE PROCESSING APPARATUS, AND IMAGE PROCESSING METHOD

CROSS-REFERENCE TO RELATED APPLICATION

This application is a Continuation Application of No. PCT/JP2013/73405, filed on Aug. 30, 2013, and the PCT application is based upon and claims the benefit of priority from Japanese Patent Application No. 2012-189917, filed on Aug. 30, 2012, and Japanese Patent Application No. 2013-179627, filed on Aug. 30, 2013, the entire contents of which are incorporated herein by reference.

FIELD

An embodiment of the present invention as an aspect of the present invention relates to an X-ray CT (computed tomography) apparatus, an image processing apparatus and an image processing method which can perform dual energy scanning or multi-energy scanning.

BACKGROUND

An X-ray CT apparatus, which provides information on a subject as images based on intensity of X-rays transmitted through the subject, plays an important role in many medical actions including diagnosis and treatment of diseases and surgical planning.

Recent X-ray CT apparatuses use a technique known as dual energy scanning. The dual energy scanning as referred to herein is a technique for acquiring images by scanning a subject using two different types of X-ray tube voltage. CT which uses dual energy scanning is referred to as "dual energy CT."

The X-ray CT apparatus which uses the dual energy scanning technique separates materials based on information obtained using two different types of X-ray tube voltage and can thereby obtain various images such as monochromatic X-ray images, density images, effective atomic number images, or artifact-free images (images with reduced artifacts). Note that the X-rays used in this case are continuous spectrum X-rays containing various energies and having a specific energy distribution.

In conventional art, various types of images are obtained using the dual energy scanning technique. However, there is a problem in that it is difficult to select one of conceivable candidate energies because plural materials are considered to be usually contained in radiographic coverage and optimum energy for diagnostic imaging varies depending on a subject's diagnosis region, materials, and the like. In determining whether or not an energy value is optimum for diagnostic imaging, factors taken into consideration include, for example, whether there are large differences in CT value, providing clear contrast or whether bones and artifacts can be removed.

Suppose, for example, an X-ray CT apparatus generates monochromatic X-ray images using the dual energy scanning technique. When soft tissue contained in radiographic coverage is diagnostically imaged, differences in CT value are large at relatively low energy, providing clear contrast and making it easy to diagnostically image the soft tissue, but the differences in CT value are small at relatively high energy, providing low contrast and making it difficult to diagnostically image the soft tissue. Thus, from the perspective of diagnostic imaging of soft tissue, relatively low energy has to be selected as optimum energy for generation of monochromatic X-ray images. On the other hand, high energy is advantageous to removal of bones and artifacts contained in radiographic coverage. Then, from the perspective of capability to remove bones and artifacts, relatively high energy has to be selected as optimum energy for generation of monochromatic X-ray images. In such cases, it is difficult to select one of conceivable candidate energies.

As another example, suppose metal artifacts (artifacts stemming from man-made objects containing metal) are produced during diagnostic imaging of soft tissue. As described above, from the perspective of diagnostic imaging of soft tissue, relatively low energy has to be selected as optimum energy for generation of monochromatic X-ray images. However, because metal artifacts are reduced at relatively high energies, from the perspective of reducing metal artifacts, relatively high energy has to be selected as optimum energy for generation of monochromatic X-ray images. This also makes it difficult to select optimum energy for generation of monochromatic X-ray images.

BRIEF DESCRIPTION OF THE DRAWINGS

In accompanying drawings,

FIG. 7 is a diagram showing a configuration example of an energy table prestored in an HDD or a memory of an image processing apparatus;

FIG. 9 is a diagram for illustrating a concept of generating a fusion image;

DETAILED DESCRIPTION

Figure 1:
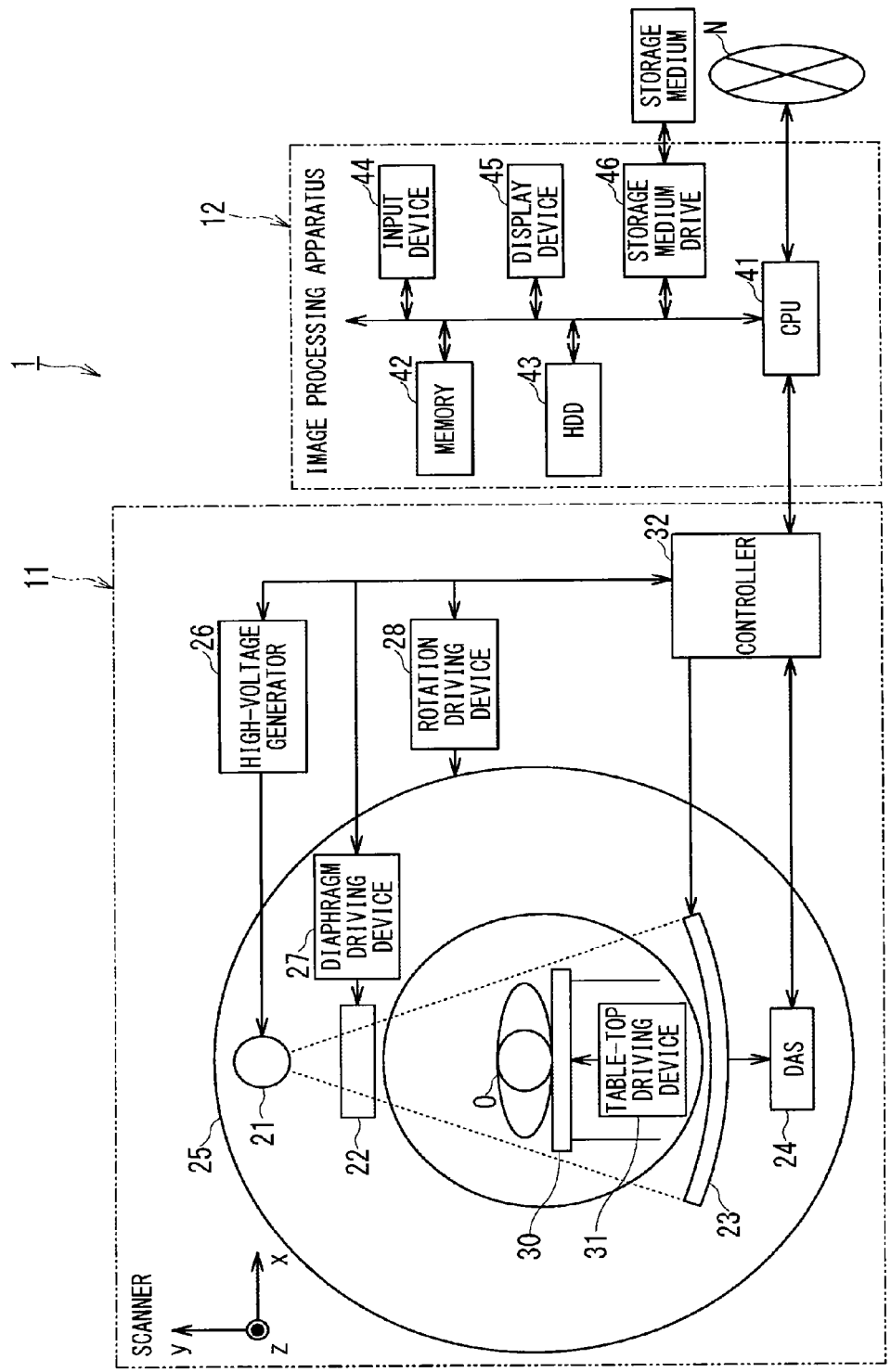
FIG. 1 is a diagram showing a configuration example of an X-ray CT apparatus according to a first embodiment.

An X-ray CT apparatus, an image processing apparatus and an image processing method according to embodiments of the present invention will be described with reference to the accompanying drawings.

To solve the above-described problems, the present embodiments provide the X-Ray CT apparatus, including: an X-ray tube configured to emit X-rays; a high-voltage power supply configured to apply an X-ray tube voltage to the X-ray tube; an X-ray detector equipped with a plurality of X-ray detecting elements and configured to detect the X-rays; an image generating unit configured to generate a plurality of reference material images corresponding to respective ones of a plurality of reference materials on a basis of pre-reconstruction data of multi-energy obtained by scanning a subject; a discrimination unit configured to discriminate each of a plurality of materials contained in an imaging region of the subject on a basis of the plurality of reference material images; a monochromatic X-ray image generating unit configured to generate a monochromatic X-ray image at energy determined by each of the plurality of discriminated materials; a combined-image generating unit configured to combine a plurality of monochromatic X-ray images corresponding to the plurality of materials and to generate a combined image; and a display unit configured to display the combined image on a display device.

To solve the above-described problems, the present embodiments provide the image processing apparatus, including: an image generating unit configured to generate a plurality of reference material images corresponding to respective ones of a plurality of reference materials on a basis of pre-reconstruction data of multi-energy obtained by scanning a subject; a discrimination unit configured to discriminate each of a plurality of materials contained in an imaging region of the subject on a basis of the plurality of reference material images; a monochromatic X-ray image generating unit configured to generate a monochromatic X-ray image at energy determined by each of the plurality of discriminated materials; a combined-image generating unit configured to combine a plurality of monochromatic X-ray images corresponding to the plurality of materials and to generate a combined image; and a display unit configured to display the combined image on a display device.

To solve the above-described problems, the present embodiments provide the image processing method, including: generating a plurality of reference material images corresponding to respective ones of a plurality of reference materials on a basis of pre-reconstruction data of multi-energy, stored in a storage, obtained by scanning a subject; discriminating each of a plurality of materials contained in an imaging region of the subject on a basis of the plurality of reference material images; generating a monochromatic X-ray image at energy determined by each of the plurality of discriminated materials; combining a plurality of monochromatic X-ray images corresponding to the plurality of materials and generating a combined image; and displaying the combined image on a display device.

The X-ray CT apparatus, an image processing apparatus and an image processing method according to the embodiments of the present invention eliminates the need to select one of conceivable candidate energies even if optimum energy for diagnostic imaging varies with a subject's diagnosis region, materials, and the like. Also, the X-ray CT apparatus, an image processing apparatus, and an image processing method according to the embodiments of the present invention can provide images with reduced artifacts and with contrast improved on a material by material basis even if the optimum energy for diagnostic imaging varies with a subject's diagnosis region, materials, and the like.

Note that the X-ray CT apparatus according to the embodiments of the present invention may be any of various types, including a rotate/rotate type in which an X-ray tube and detector rotate as a single unit around the subject and a stationary/rotate type in which a large number of detecting elements are arranged to form a ring and only an X-ray tube rotates around the subject. In the description of the embodiments of the present invention, it is assumed that the X-ray CT apparatus is of the rotate/rotate type which is currently in the mainstream.

An X-ray CT apparatus according to a first embodiment which is an example of the X-ray CT apparatuses according to the embodiments of the present invention uses dual energy scanning which is a technique for acquiring images by scanning a subject using plural different types of X-ray tube voltage. Radiographic methods by the dual energy scanning is broadly divided into at least three methods. A first method is a "Slow-kV switching method" (double rotation method) which involves taking a radiograph at a first X-ray tube voltage and then taking a radiograph at a second X-ray tube voltage different from the first X-ray tube voltage, using a single X-ray tube. A second method is a "Fast-kV switching method" (high-speed switching method) which involves taking radiographs by rapidly switching the X-ray tube voltage of the X-ray tube on a view by view basis during rotation (scanning). In this case, a data acquisition system acquires data in synchronization with the switching of the X-ray tube voltage, acquiring the data at different X-ray tube voltages in a single scan. A third method is a "dual source system (dual lamp system)" which involves taking radiographs at different X-ray tube voltages using two X-ray tubes rather than a single X-ray tube. A fourth method is a "multilayer system" which uses X-ray detectors of multilayered structure. For example, when an X-ray detectors (detector in a shallow layer and detector in a deep layer) of a two-layer structure are used, low-energy X-rays are detected by the detector in the shallow layer and high-energy X-rays passing through the shallow layer is detected by the detector in the deep layer. The present invention is applicable to any of the types. In the description of the embodiments of the present invention, it is assumed that the second method is used.

Furthermore, the X-ray CT apparatus according to the first embodiment will be described citing a case in which pre-reconstruction data (raw data or projection data) of dual energy is acquired using dual energy scanning, but the present invention is also applicable to a case in which pre-reconstruction data of multi-energy is acquired using multi-energy scanning higher than the dual energy scan.

In addition, an X-ray CT apparatus according to a second embodiment as one of the X-ray CT apparatus according to the embodiments of the present invention will be described citing a case in which pre-reconstruction data of dual energy is acquired using single energy scanning, but the present invention is also applicable to a case in which pre-reconstruction data of multi-energy is acquired using single energy scanning.

First Embodiment

FIG. 1 is a diagram showing a configuration example of an X-ray CT apparatus 1 according to a first embodiment.

FIG. 1 shows the X-ray CT apparatus 1 according to the first embodiment which performs dual energy scanning. The X-ray CT apparatus 1 is mainly made up of a scanner 11 and an image processing apparatus (console) 12. The scanner 11 of the X-ray CT apparatus 1 is normally installed in an examination room and used to generate X-ray transmission data on a patient O (subject). On the other hand, the image processing apparatus 12 is normally installed in a control room next to the examination room and used to generate projection data based on the transmission data and generate and display a reconstructed image.

The scanner 11 of the X-ray CT apparatus 1 includes an X-ray tube 21, a diaphragm 22, an X-ray detector 23, a DAS (data acquisition system) 24, a rotary unit 25, a high-voltage generator 26, a diaphragm driving device 27, a rotation driving device 28, a table-top 30, a table-top driving device 31, and a controller 32.

The X-ray tube 21 generates X-rays by bombarding a metal target with an electron beam at an X-ray tube voltage supplied from the high-voltage generator 26 and directs the X-rays onto the X-ray detector 23. An X-ray fan beam or X-ray cone beam is generated from the X-rays radiated from the X-ray tube 21. Electric power necessary for X-ray irradiation is supplied to the X-ray tube 21 from the high-voltage generator 26 under the control of the controller 32.

Being driven by the diaphragm driving device 27, the diaphragm 22 adjusts an irradiation range of the X-rays from the X-ray tube 21 in an x-axis direction and z-axis direction (slice direction). That is, by adjusting an opening of the diaphragm 22 using the diaphragm driving device 27, it is possible to change the X-ray irradiation range in the slice direction.

The X-ray detector 23 is a one-dimensional array-type detector which has plural detecting elements in a channel direction and a single detecting element in a column (slice) direction. Alternatively, the X-ray detector 23 may be a two-dimensional array detector (also referred to as a multi-slice detection), which is arranged in a matrix with plural detecting elements both in the channel direction and slice direction. The X-ray detector 23 detects the X-rays radiated from the X-ray tube 21 and transmitted through the patient O.

The DAS 24 acquires data in synchronization with switching of the X-ray tube voltage during dual energy scanning. The DAS 24 amplifies a signal of the transmission data (X-ray detection data) detected by each detecting element of the X-ray detector 23 and converts the signal into a digital signal. Output data of the DAS 24 is supplied to the image processing apparatus 12 via the controller 32 of the scanner 11. Details of the DAS 24 will be described later.

The rotary unit 25 holds the X-ray tube 21, diaphragm 22, X-ray detector 23, DAS 24, and diaphragm driving device 27 as an integral unit. With the X-ray tube 21 and X-ray detector 23 opposed to each other, the rotary unit 25 is configured to be able to rotate the X-ray tube 21, diaphragm 22, X-ray detector 23, DAS 24, and diaphragm driving device 27 as an integral unit around the patient O. The high-voltage generator 26 may be configured to be held by the rotary unit 25. Incidentally, a direction parallel to a rotation center axis of the rotary unit 25 is defined as the z-axis direction, and a plane orthogonal to the z-axis direction is defined by the x-axis direction and a y-axis direction.

The high-voltage generator 26 supplies electric power necessary for dual energy scanning to the X-ray tube 21 under the control of the controller 32.

Figure 2:
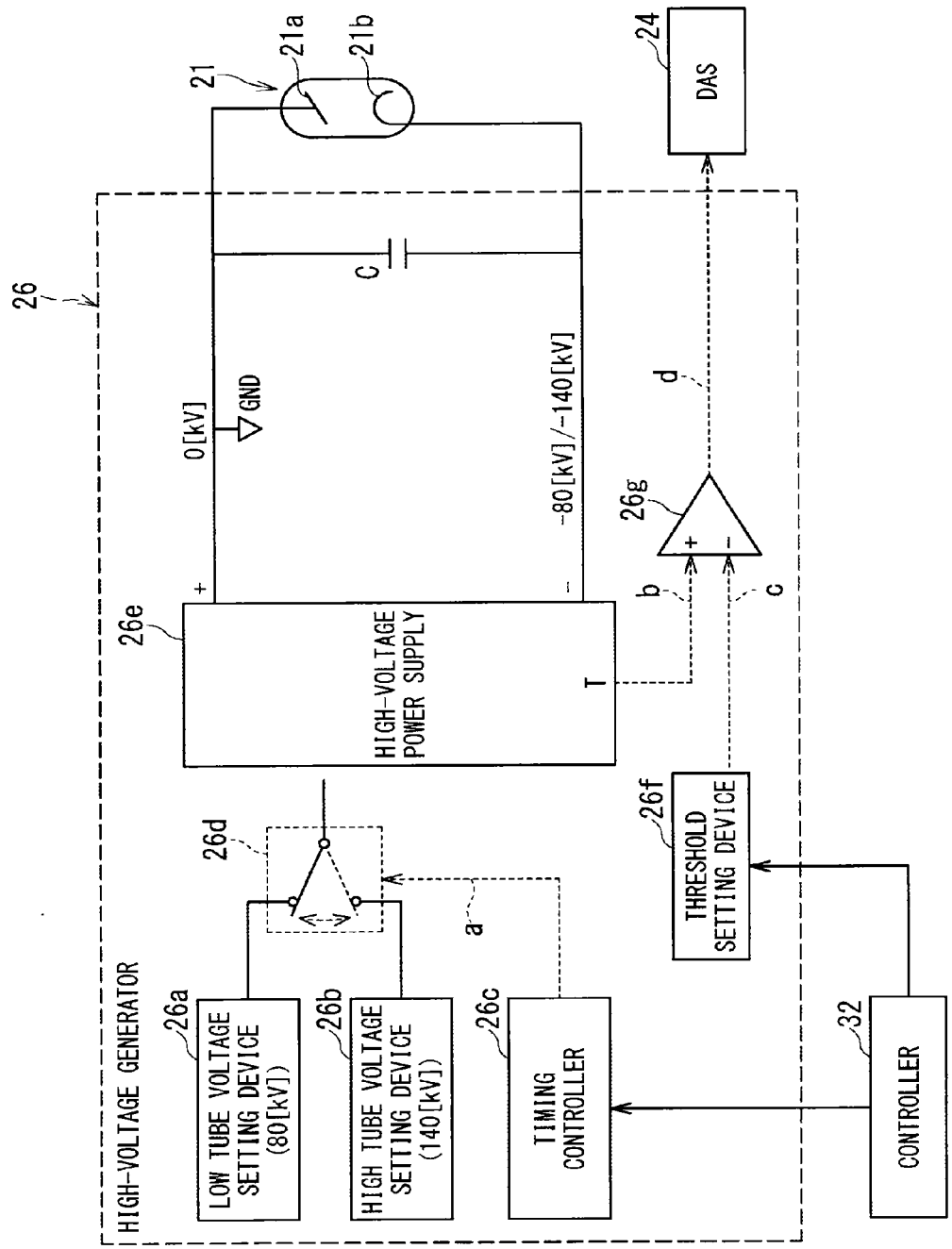
FIG. 2 is a diagram showing a configuration example of an X-ray tube and a high voltage power supply installed on the X-ray CT apparatus according to the first embodiment.

FIG. 2 is a diagram showing a configuration example of the X-ray tube 21 and high-voltage generator 26 installed on the X-ray CT apparatus 1 according to the first embodiment.

As shown in FIG. 2, the X-ray tube 21 includes an anode 21a and a filament (cathode) 21b. Also, the high-voltage generator 26 includes a low tube voltage setting device 26a, a high tube voltage setting device 26b, a timing controller 26c, a switch 26d, a high-voltage power supply 26e, a threshold setting device 26f, a comparator 26g, and a capacitor C. In the following description, it is assumed that High-kV (high X-ray tube voltage) is 140 kV and Low-kV (low X-ray tube voltage) is 80 kV in dual energy scanning, but this is not restrictive, and any combination of a high X-ray tube voltage and low X-ray tube voltage may be used. High-kV (high X-ray tube voltage) in dual energy scanning is defined as a "first X-ray tube voltage" and Low-kV (low X-ray tube voltage) is defined as a "second X-ray tube voltage."

The low tube voltage setting device 26a sets Low-kV while the high tube voltage setting device 26b sets High-kV. Output of either the tube voltage setting device 26a or 26b can be selected. The output of the tube voltage setting device 26a or 26b is connected to the high-voltage power supply 26e via the switch 26d controlled by the timing controller 26c. The switch 26d is controlled by a signal "a" outputted from the timing controller 26c. The low tube voltage setting device 26a is selected when the signal "a" indicates "L" while the high tube voltage setting device 26b is selected when the signal "a" indicates "H."

A positive side output of the high-voltage power supply 26e is electrically connected to the anode 21a of the X-ray tube 21 and grounded. Also, a negative side output of the high-voltage power supply 26e is electrically connected to the filament 21b of the X-ray tube 21. The output of the high-voltage power supply 26e is switched to Low-kV or High-kV (e.g., the X-ray tube voltage 80 kV or 140 kV), timed with switching in response to the signal "a". The high-voltage power supply 26e is equipped with a tube voltage detecting terminal T, which is connected to a positive side input of the comparator 26g. The threshold setting device 26f is connected to a negative side input of the comparator 26g.

The comparator 26g accepts input of a signal "b" from the tube voltage detecting terminal T of the high-voltage power supply 26e and input of a signal "c" from the threshold setting device 26f, and outputs a signal "d" to the DAS 24, indicating "L" when the signal "b" is larger than the signal "c" or indicating "H" when the signal "b" is equal to or smaller than the signal "c". When the signal "d" indicates "L," the DAS 24 determines that the data is transmission data at Low-kV, and when the signal "d" indicates "H," the DAS 24 determines that the data is transmission data at High-kV.

In accordance with a tube voltage control signal from a tube voltage control unit 51 of a CPU 41 described later in FIG. 4, the controller 32 performs dual energy scanning by controlling switching operation of the switch 26d via the timing controller 26c of the high-voltage generator 26 and selects whether to cause the high-voltage power supply 26e to output Low-kV set by the low tube voltage setting device 26a or output High-kV set by the high tube voltage setting device 26b. In response to a control signal from the controller 32, the switch 26d gives a selected tube voltage setting signal to the high-voltage power supply 26e.

The controller 32 also sends a control signal to the DAS 24. The DAS 24 recognizes whether data acquired by dual energy scanning is produced by Low-kV X-ray irradiation or High-kV X-ray irradiation.

Returning to the description of FIG. 1, the diaphragm driving device 27 has a mechanism for adjusting the X-ray irradiation range in the x-axis direction and z-axis direction via the diaphragm 22 under the control of the controller 32.

The rotation driving device 28 has a mechanism for rotating the rotary unit 25 so as to rotate around a cavity by maintaining their positional relationship, under the control of the controller 32.

The table-top 30 allows the patient O to be placed thereon.

The table-top driving device 31 has a mechanism for causing the table-top 30 to move up and down along the y-axis direction and move forward and backward along the z-axis direction, under the control of the controller 32. The rotary unit 25 has an opening in a central portion and the patient O placed on the table-top 30 is inserted through the opening.

The controller 32 includes a CPU (central processing unit), memory, and the like (none is shown). On instructions from the image processing apparatus 12, the controller 32 controls the X-ray detector 23, DAS 24, high-voltage generator 26, diaphragm driving device 27, rotation driving device 28, table-top driving device 31, and the like so as to perform dual energy scanning.

The image processing apparatus 12 of the X-ray CT apparatus 1 is configured based on a computer and is capable of intercommunicating with a network (local area network) N. The image processing apparatus 12 is mainly made up of basic hardware, including a CPU 41, a memory 42, an HDD (hard disc drive) 43, an input device 44, and a display device 45. The CPU 41 is interconnected with each hardware component of the image processing apparatus 12 via a bus serving as a common signal transmission path. Note that the image processing apparatus 12 may sometimes be equipped with a storage media drive 46.

The CPU 41 is a control apparatus configured as an integrated circuit (LSI) in which an electronic circuit made up of semiconductors are enclosed in a package having plural terminals. When an operator such as a doctor enters a command by operating the input device 44, the CPU 41 executes a program stored in the memory 42. Alternatively, the CPU 41 executes a program stored in the HDD 43, a program installed on the HDD 43 by being transferred from the network N, or a program installed on the HDD 43 by being read out of an recording medium mounted in the storage media drive 46, where the program is executed by being loaded into the memory 42.

The memory 42 is a storage device including a ROM (read only memory), a RAM (random access memory), and the like. The memory 42 stores IPL (initial program loading), BIOS (basic input/output system), and data, and is used as a work memory for the CPU 41 or used to temporarily store data.

The HDD 43 is a storage device configured with an unremovable built-in metal disk to which magnetic material has been applied by coating or vapor deposition. The HDD 43 is a storage device adapted to store data as well as programs installed on the image processing apparatus 12, where the programs include application programs, an OS (operating system), and the like. Also, the OS may provide GUI (graphical user interface) which uses a lot of graphics in displaying information on the display device 45 for an operator such as a surgeon and allows basic actions to be performed via the input device 44.

The input device 44 is a pointing device configured to be operated by the operator and send an input signal to the CPU 41 according to an operator action.

The display device 45 includes an image composition circuit, a VRAM (video random access memory), a display, and the like (none is shown). The image composition circuit generates composite data by combining image data with character data of various parameters. The VRAM presents composite data on the display. The display is a liquid crystal display, CRT (cathode ray tube), or the like, which displays images one after another.

Figure 3:
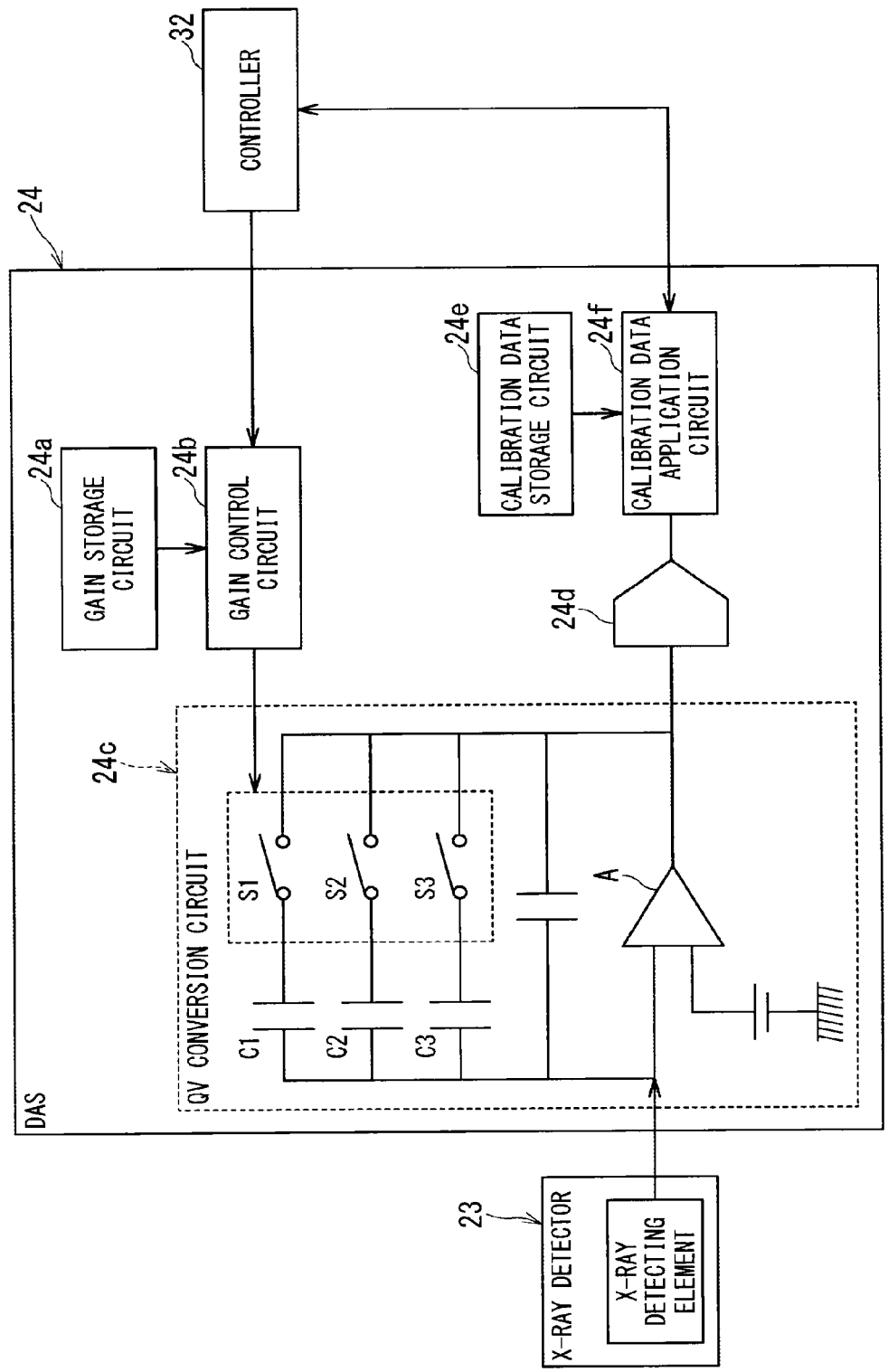
FIG. 3 is a diagram showing a configuration example of a DAS installed on the X-ray CT apparatus according to the first embodiment.

FIG. 3 is a diagram showing a configuration example of the DAS 24 installed on the X-ray CT apparatus 1 according to the first embodiment.

As shown in FIG. 3, the DAS 24 includes a gain storage circuit 24a, a gain control circuit 24b, a QV conversion circuit (integrating circuit and gain variable amplifier circuit) 24c, an A/D conversion circuit 24d, a calibration data storage circuit 24e, and a calibration data application circuit 24f. It is assumed hereinafter that each X-ray detecting element of the X-ray detector 23 has the circuits 24a to 24f, but each X-ray detecting element group made up of plural X-ray detecting elements may be provided with the circuits 24a to 24f.

The gain storage circuit 24a prestores gains (amplification factors). The gain storage circuit 24a prestores a gain corresponding to a size of the head for head radiography, a gain corresponding to a size of the chest for chest radiography, and a gain corresponding to a size of the stomach for stomach radiography. The gain storage circuit 24a may also store gains in such a way as to allow images of plural regions differing in body diameter to be acquired by a single X-ray irradiation.

Under the control of the controller 32, the gain control circuit 24b controls the QV conversion circuit 24c so as to set a gain stored in the gain storage circuit 24a.

In synchronization with an X-ray irradiation period, the QV conversion circuit 24c periodically integrates a voltage signal outputted from an X-ray detecting element $E_{m,n}$ in an nth column on an mth channel of the X-ray detector 23. Also, the QV conversion circuit 24c includes an operational amplifier A, three capacitors C (C1, C2, and C3) differing in capacitance, and three switches S (S1, S2, and S3). The switches S1, S2, and S3 are associated with the capacitors C1, C2, and C3, respectively, and on-off controlled by the gain control circuit 24b. The QV conversion circuit 24c can set six gains using combinations of ONs and OFFS of the capacitors C1, C2, and C3. Note that to set six gains, the QV conversion circuit 24c may be equipped with six capacitors C equal in capacitance. Also, the number of capacitors C included in the QV conversion circuit 24c is not limited to three and six.

Using a gain controlled by the gain control circuit 24b, the QV conversion circuit 24c amplifies transmission data outputted by the X-ray detecting element $E_{m,n}$.

The A/D conversion circuit 24d converts analog data outputted by the QV conversion circuit 24c into digital data.

The calibration data storage circuit 24e stores correct calibration data obtained beforehand as data for calibration through dual energy scanning under the control of the controller 32. The calibration data stored in the calibration data storage circuit 24e will be described.

The calibration data application circuit 24f applies calibration data stored in the calibration data storage circuit 24e to output data of the A/D conversion circuit 24d produced as a result of the dual energy scanning. The calibration data application circuit 24f recognizes an X-ray tube voltage pair of data acquired through the dual energy scanning as well as values of X-ray tube current in a tube current modulation. The calibration data application circuit 24f acquires calibration data corresponding to the recognized X-ray tube voltage pair and tube current values from the calibration data storage circuit 24e and applies the acquired calibration data to an output signal of the A/D conversion circuit 24d.

When the calibration data storage circuit 24e has a plurality of pieces of calibration data related to respective discrete values of the tube current, the calibration data application circuit 24f interpolates a piece of calibration data related to non-existent value of the tube current and thereby applies an interpolated piece of calibration data.

Returning to the description of FIG. 1, the image processing apparatus 12 applies a logarithmic conversion process or a correction process (pre-processing) such as sensitivity correction to raw data of dual energy received from the DAS 24 of the scanner 11, thereby generates projection data, and stores the projection data in a storage device such as the HDD 43. Also, the image processing apparatus 12 removes scattered radiation from the pre-processed projection data. The image processing apparatus 12 removes the scattered radiation on the basis of values of the projection data in an X-ray exposure range, and makes scattered radiation correction by subtracting the scattered radiation estimated from magnitude of value of projection data to be subjected to scattered radiation correction or adjacent projection data from the projection data to be corrected. The image processing apparatus 12 generates image data based on the corrected projection data and stores the image data in a storage device such as the HDD 43 or displays the image data on the display device 45.

Figure 4:
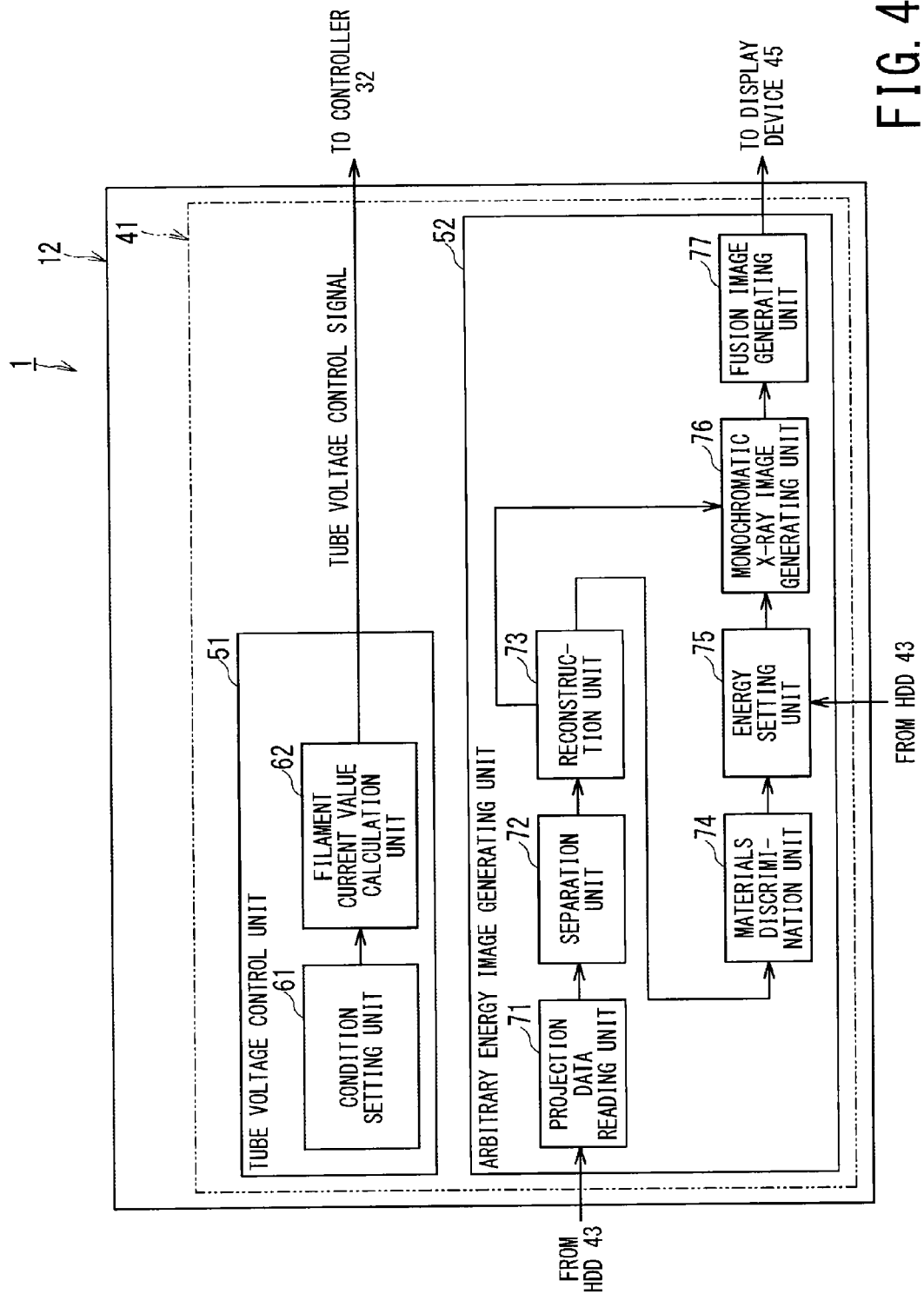
FIG. 4 is a block diagram showing functions of the X-ray CT apparatus according to the first embodiment.

FIG. 4 is a block diagram showing functions of the X-ray CT apparatus 1 according to the first embodiment.

As the CPU 41 of the image processing apparatus 12 shown in FIG. 1 executes a program, the X-ray CT apparatus 1 functions as a tube voltage control unit 51 and an arbitrary energy image generating unit 52 as shown in FIG. 4. Specifically, the tube voltage control unit 51 includes a condition setting unit 61 and a filament current value calculation unit 62. Also, the arbitrary energy image generating unit 52 includes a projection data reading unit 71, a separation unit 72, a reconstruction unit 73, a materials discrimination unit 74, an energy setting unit 75, a monochromatic X-ray image generating unit 76, and a fusion image generating unit 77. Note that all or part of the tube voltage control unit 51 and arbitrary energy image generating unit 52 of the image processing apparatus 12 may be provided as hardware on the image processing apparatus 12. Also, all or part of the tube voltage control unit 51 and arbitrary energy image generating unit 52 of the image processing apparatus 12 may be provided not only on the image processing apparatus 12, but also on the high-voltage generator 26 and controller 32.

First, configuration of the tube voltage control unit 51 will be described. The tube voltage control unit 51 generates a tube voltage control signal intended to switch the tube voltage generated by the high-voltage generator 26 and control switching conditions and supplies the generated tube voltage control signal to the controller 32.

The condition setting unit 61 of the tube voltage control unit 51 has a function to set a tube current condition (maximum tube current value during modulation) based on a scan plan, information obtained from a positioning image (scout image) prior to a scan, or X-ray transmission data transmitted through the subject during scanning. Also, the condition setting unit 61 has a function to set a condition for modulating a dose of X-ray radiation in time series on the basis of a scan plan, information obtained from a scout image, or X-ray transmission data transmitted through the subject during scanning. Examples of modulation include periodic modulation with respect to a rotation angle (rotation angle modulation), modulation in the z-axis direction (z-axis modulation), periodic modulation in synchronization with an electrocardiograph signal (electrocardiograph-synchronized modulation), modulation intended to reduce radiation exposure of hypersensitive regions such as the eyeballs and ovary (hypersensitive region modulation), and combinations thereof. The tube current condition and modulation condition set by the condition setting unit 61 are sent to the filament current value calculation unit 62.

The filament current value calculation unit 62 has a function to calculate a filament current value of the X-ray tube 21 via the controller 32 and high-voltage generator 26 on the basis of the tube current condition and modulation condition set by the condition setting unit 61. Also, the filament current value calculation unit 62 has a function to supply the calculated filament current value to a filament of the X-ray tube 21.

Next, configuration of the arbitrary energy image generating unit 52 will be described. The arbitrary energy image generating unit 52 generates an arbitrary energy image for each material existing in radiographic coverage using an appropriate energy. When the arbitrary energy image generating unit 52 generates an arbitrary energy image, the X-ray CT apparatus 1 according to the first embodiment performs dual energy scanning to acquire projection data of dual energy. Examples of methods for dual energy scanning include a "Fast-kV switching method" (method switching method) which involves taking radiographs by rapidly switching the X-ray tube voltage of the X-ray tube on a view by view basis during rotation (scanning).

The projection data reading unit 71 of the arbitrary energy image generating unit 52 reads the projection data of dual energy as pre-reconstruction data out of the HDD 43 of the image processing apparatus 12. The projection data reading unit 71 supplies the projection data of dual energy which has been read out to the separation unit 72. Note that the projection data reading unit 71 may read raw data as pre-reconstruction data instead of the projection data.

The separation unit 72 separates (discriminates) a plurality of predetermined reference materials (contrast medium, $CaCo_3$, uric acid, fat, and the like) existing in the radiographic coverage using the projection data of dual energy obtained from the projection data reading unit 71. In the following description, it is assumed that the separation unit 72 separates two reference materials and generates two sets of projection data corresponding to the respective reference materials, but the number of reference materials is not limited to two as long as the number is two or more. The separation unit 72 supplies the two sets of projection data corresponding to the respective ones of the two separated reference materials to the reconstruction unit 73. A method used by the separation unit 72 to separate reference materials will be described in detail later with reference to a flowchart of FIG. 5.

The reconstruction unit 73 reconstructs a reference material image (reference material weighted image) as image data for each reference material on the basis of the two sets of projection data corresponding to the respective ones of the two reference materials separated by the separation unit 72. The reconstruction unit 73 generates a reference material image of reference material 1 based on the set of projection data corresponding to reference material 1 and generates a reference material image of reference material 2 based on the set of projection data corresponding to reference material 2. By combining the plural reference material images generated by the reconstruction unit 73, it is possible to generate plural monochromatic X-ray images as multiple items of image data corresponding to plural energies. The reconstruction unit 73 supplies the two generated reference material images corresponding to the respective ones of the two reference materials to the materials discrimination unit 74 and monochromatic X-ray image generating unit 76.

Using the two reference material images generated by the reconstruction unit 73 for the respective ones of the two reference materials, the materials discrimination unit 74 discriminates (identifies) materials (including tissue, contrast medium, bone, and the like) existing in the radiographic coverage and supplies results of the discrimination to the energy setting unit 75. A method used by the materials discrimination unit 74 to discriminate materials will be described in detail later with reference to a flowchart of FIG. 5.

On the basis of the results of discrimination from the materials discrimination unit 74 and with reference to an energy table prestored in the HDD 43 or memory 42 of the image processing apparatus 12, the energy setting unit 75 sets an energy at which a monochromatic X-ray image for each material existing in the radiographic coverage will be generated. The energy setting unit 75 supplies data on the set energy to the monochromatic X-ray image generating unit 76.

On the basis of the energy set for each material by the energy setting unit 75 and the two reference material images generated by the reconstruction unit 73 for the respective ones of the two reference materials, the monochromatic X-ray image generating unit 76 generates a monochromatic X-ray image for each material existing in the radiographic coverage. Incidentally, the term "monochromatic X-ray image" used in the first embodiment means an image which is created based on the projection data obtained by taking a radiograph using continuous spectrum X-rays with specific effective X-ray energy and which is equivalent to an image obtained by taking a radiograph using monochromatic X-rays of a specific energy. The monochromatic X-ray image generating unit 76 supplies data on the generated monochromatic X-ray image to the fusion image generating unit 77.

The fusion image generating unit 77 generates a fusion image using the monochromatic X-ray image generated by the monochromatic X-ray image generating unit 76.

Next, a fusion image display process of the X-ray CT apparatus 1 according to the first embodiment will be described.

Figure 5:
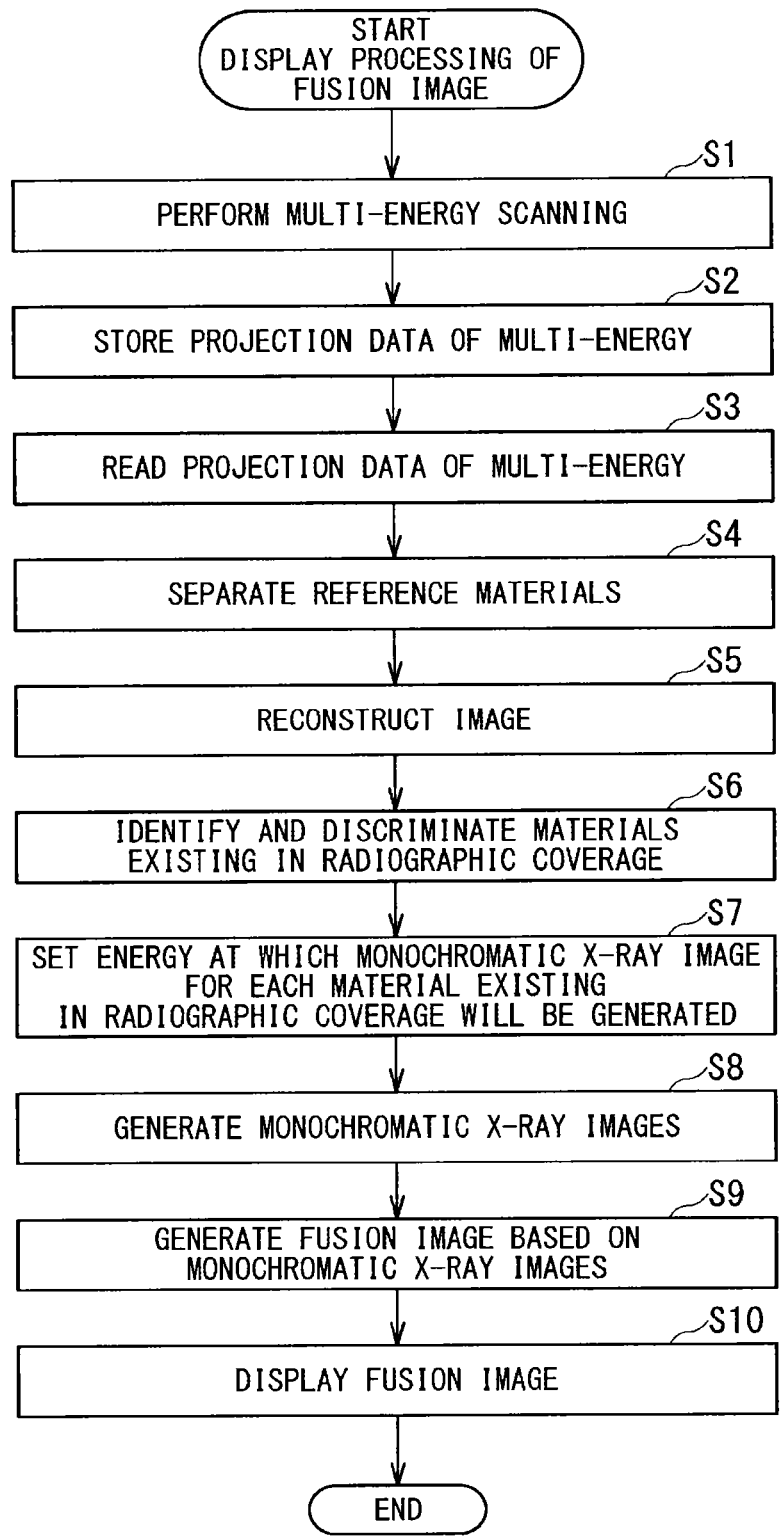
FIG. 5 as a flowchart showing an operation of the X-ray CT apparatus according to the first embodiment.

FIG. 5 is a flowchart showing an operation of the X-ray CT apparatus 1 according to the first embodiment.

In step S1, the scanner 11 of the X-ray CT apparatus 1 performs dual energy scanning under the control of the controller 32, and acquires projection data via the dual energy scanning (e.g., a Fast-kV switching method (high speed switching method)). Specifically, the scanner 11 takes radiographs by rapidly switching the X-ray tube voltage of the X-ray tube on a view by view basis during rotation (scanning) and radiographs the subject O using two different types of X-ray tube voltage: High-kV (high X-ray tube voltage) and Low-kV (low X-ray tube voltage). Note that the X-ray CT apparatus 1 can use a multi-energy scan higher than the dual energy scan. For example, in the case of triple energy scanning, the subject O is radiographed using three different types of X-ray tube voltage.

In step S2, the DAS 24 of the scanner 11 acquires data in synchronization with switching of the X-ray tube voltage during dual energy scanning and amplifies a signal of the transmission data detected by each detecting element of the X-ray detector 23 and converts the signal into a digital signal. Output data of the DAS 24 is supplied to the image processing apparatus 12 via the controller 32 of the scanner 11.

Then, the CPU 41 of the image processing apparatus 12 of the X-ray CT apparatus 1 acquires raw data of dual energy inputted by the DAS 24 of the scanner 11, applies a logarithmic conversion process or a correction process (pre-processing) such as sensitivity correction to the acquired raw data, thereby generates projection data, and stores the projection data in a storage device such as the HDD 43. Under the control of the CPU 41, the HDD 43 stores the projection data of dual energy.

In step S3, the projection data reading unit 71 of the arbitrary energy image generating unit 52 of the CPU 41 reads the projection data of dual energy stored in the HDD 43 of the image processing apparatus 12. The projection data reading unit 71 supplies the projection data which has been read out to the separation unit 72.

In step S4, the separation unit 72 separates the two reference materials existing in the radiographic coverage using the projection data of dual energy from the projection data reading unit 71. The separation unit 72 supplies the two sets of projection data corresponding to the respective ones of the two separated reference materials to the reconstruction unit 73.

In step S5, the reconstruction unit 73 reconstructs a reference material image (reference material weighted image) as image data for each reference material on the basis of the two sets of projection data corresponding to the respective ones of the two reference materials separated by the separation unit 72. The reconstruction unit 73 generates a reference material image of the first reference material on the basis of the set of projection data corresponding to the first reference material and generates a reference material image of the second reference material on the basis of the set of projection data corresponding to the second reference material. By combining the plural reference material images generated by the reconstruction unit 73, it is possible to generate plural monochromatic X-ray images as multiple items of image data corresponding to plural energies. The reconstruction unit 73 supplies the two generated reference material images corresponding to the respective ones of the two reference materials to the materials discrimination unit 74 and monochromatic X-ray image generating unit 76.

In step S6, using the two reference material images generated by the reconstruction unit 73 for the respective ones of the two reference materials, the materials discrimination unit 74 discriminates the materials existing in the radiographic coverage. Now, concepts of methods of separating and discriminating the reference materials existing in the radiographic coverage will be described.

First, the concept of methods of identifying the materials existing in the radiographic coverage will be described. Methods of identifying materials using data on dual energy are largely divided into an image-based method which identifies materials using the image itself generated from the projection data of dual energy (Non-Patent Document: Johnson TR. Et al., "Material differentiation by dual energy CT: initial experience", Eur Radiol (2007), 17, 1510-1517) and a raw-data-based method which separates the projection data of dual energy into two reference materials, creates images based on the respective reference materials, and thereby identifies materials using the created images (Patent Document: Japanese Patent Application Publication (Laid-open: KOKAI) No. 2009-261942 A). The present invention is applicable to both methods, but it is assumed that the latter method is used in the first embodiment. Of course, a method other than those described above may be used as long as the method can identify materials.

The separation unit 72 separates the projection data of dual energy on the basis of the two reference materials. A separation method using the two reference materials is described in Patent Document 1 described above. For example, assuming any given material made up of two reference materials, suppose an X-ray attenuation coefficient (E, x, y) acquired for the given material is to be expressed by a sum of X-ray attenuation coefficients (linear attenuation coefficients) of the two reference materials. Note that meaning of assuming that the given material is made up of the two reference materials mainly lies in that the X-ray attenuation coefficient $\mu$ (E, x, y) acquired for the given material is expressed by the sum (linear combination) of the X-ray attenuation coefficients (linear attenuation coefficients) of the two reference materials using a mathematical expression, and it is not assumed that the given material is actually made up of the two reference materials in a physical sense. This method allows the X-ray attenuation coefficient $\mu$ (E, x, y) of any material to be separated into the sum of the X-ray attenuation coefficients (linear attenuation coefficients) of the two reference materials.

The reconstruction unit 73 reconstructs the projection data separated in this way and thereby generates two reconstructed images. On the basis of the two reconstructed images, $c_1$ (x, y) and $c_2$ (x, y) are derived, where $c_1$ (x, y) and $c_2$ (x, y) represent abundance ratios of reference material 1 and reference material 2 of a pixel (or voxel) at (x, y). In other words, $c_1$ (x, y) and $c_2$ (x, y) represent how closely the given material resembles reference material 1 and reference material 2.

In this case, the X-ray attenuation coefficient $\mu$ (E, x, y) acquired for the given material is expressed by Eq. (1) below.

$$\mu(E,x,y)=\mu_1(E)c_1(x,y)+\mu_2(E)c_2(x,y) \quad (1)$$

The member "E" in Eq. (1) above represents X-ray energy. The members "$\mu_1$ (E)" and "$\mu_2$ (E)" represent the linear attenuation coefficients of reference materials 1 and 2, respectively at energy E.

Next, a concept of methods of discriminating the materials after acquisition of information on $c_1$ (x, y) and $c_2$ (x, y) will be described. To determine what kind of material the given material is, a correlation between $c_1$ (x, y) and $c_2$ (x, y) is used. Let us assume, for example, that reference material 1 is a contrast medium 50 [mgI/ml] while reference material 2 is water. Then, after calculation of $c_1$ (x, y) and $c_2$ (x, y) in a process of separating the reference materials, a graph is created by plotting $c_1$ on a y-axis on a pixel by pixel basic or on a voxel by voxel basic, and taking $c_2$ on an x-axis. The graph is shown in FIG. 6.

Although $c_1$ is taken as the y-axis and $c_2$ is taken as the x-axis as an example in the first embodiment, conversely $c_1$ may be the x-axis with $c_2$ taken as the y-axis. Another coordinate system such as an oblique coordinate system may be used instead of an orthogonal coordinate system. Furthermore, the coordinate system may be rotated at a predetermined angle around an origin or the two axes may be transformed by multiplying $c_1$ and $c_2$ by a coefficient. That is, it is sufficient if a linearly combined image can represent a correlation between two reference material images, and the present invention is applicable to any diagram which expresses the correlation between $c_1$ and $c_2$.

Figure 6:
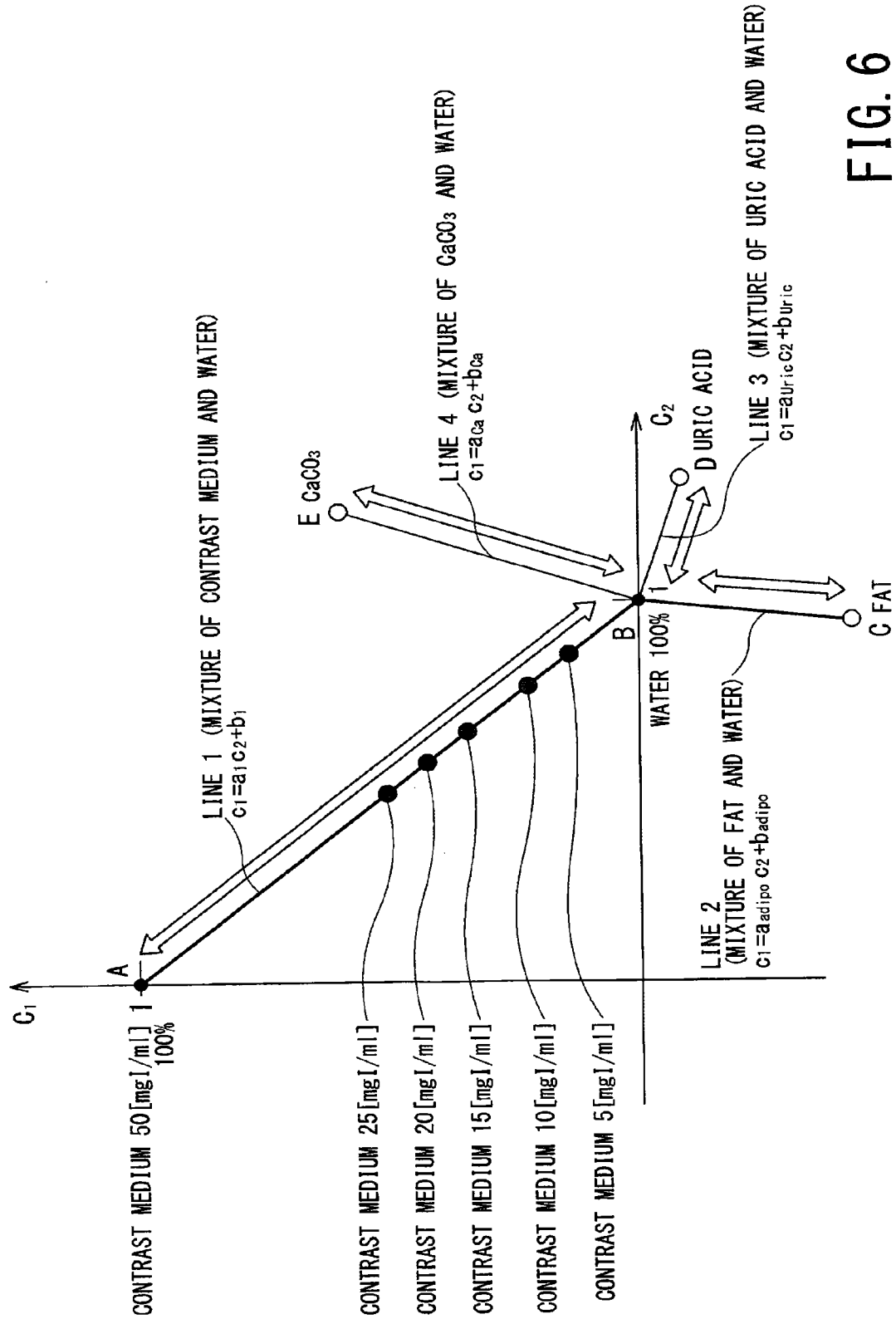
FIG. 6 is a diagram graphically showing an example of a contrast medium, fat, uric acid and calcium carbonate ($CaCO_3$) which results from calcification to explain a correlation between $c_1(x, y)$ and $c_2(x, y)$.

FIG. 6 graphically represents a contrast medium, fat, uric acid and calcium carbonate ($CaCO_3$) which results from calcification, as reference materials by way of example. As described above, suppose an X-ray attenuation coefficient $\mu$ (E, x, y) acquired for a given material is to be expressed by a sum of the X-ray attenuation coefficients (linear attenuation coefficients) of two reference materials, namely, a contrast medium 50 [mgI/ml] and water. Note that when a given material is broken down on the basis of two reference materials, $c_1$ (x, y) and $c_2$ (x, y) can take values larger than 1 depending on the given material.

For example, when the contrast medium 50 [mgI/ml], which is one of the reference materials, is expressed by the sum of the X-ray attenuation coefficients (linear attenuation coefficients) of two reference materials, namely, the contrast medium 50 [mgI/ml] and water, since the contrast medium 50 [mgI/ml] has a concentration of 100%, $c_1$=1 and $c_2$=0. The contrast medium 50 [mgI/ml] with a concentration of 100% is represented by point A. On the other hand, when water, which is one of the reference materials, is expressed by the sum of the X-ray attenuation coefficients (linear attenuation coefficients) of the two reference materials, namely, the contrast medium 50 [mgI/ml] and water, since the water has a concentration of 100%, $c_1$=0 and $c_2$=1. Water with a concentration of 100% is represented by point B. Therefore, a mixture of contrast medium and water are represented by points on straight line 1 linking point A and point B. Straight line 1 having such a correlation is represented by a linear equation $c_1 = a_1 c_2 + b_1$.

Similarly, linear equations which represent correlations between water and fat, between water and uric acid, and between water and calcium carbonate can be determined. For example, a mixture of fat and water is represented by a point on straight line 2 linking point B and point C. Note that although linear equations which represent correlations between water and another material are determined in the first embodiment for sake of convenience, this is not restrictive. A linear equation which represents a correlation with a material represented by any of points may be determined.

By capitalizing on the fact that such a correlation holds, materials can be discriminated on the basis of information on $c_1$ (x, y) and $c_2$ (x, y). That is, the correlation lines determined above represent a mixture of respective materials with water. In other words, a different straight line indicates that a different material is contained in the mixture, and this allows materials to be separated. Furthermore, on the basis of what part of what straight line the point represented by $c_1$ (x, y) and $c_2$ (x, y) is located in, it is possible to determine what kind of material it is.

For example, in the case of a mixture of a contrast medium and water, since the reference materials are water and the contrast medium, it is possible to determine, from a straight line 1 ($c1 = a_1 c_2 + b_1$) with a slope of $a_1 = -1$ and an intercept of $b_1 = 1$, that this is a mixture of a contrast medium and water and what is the mixing ratio between the contrast medium and water. Also, in the case of a mixture of calcium carbonate ($CaCO_3$) and water, it is possible to determine, from a straight line 4 with a slope of $a_{Ca} = 0.9$ and an intercept of $b_{Ca} = 0.9$, that this is a mixture of calcium carbonate and water and what is the mixing ratio between the calcium carbonate and water.

Note that two reference materials are used in the description of the first embodiment, a material may be discriminated using three or more reference materials. This will allow a material to be discriminated at a higher resolution.

Also, to obtain equations for straight lines such as shown in FIG. 6, a method is conceivable which radiograph known materials beforehand using dual energy data, acquires a linear equation for each material, stores the linear equation in a tabular form by associating the linear equation with the material, and refers to the linear equations when discriminating a material. Furthermore, to obtain projection data of dual energy a method is available for calculating equations for straight lines such as shown in FIG. 6 using linear attenuation coefficients.

The latter method, which uses linear attenuation coefficients, will be described. The linear attenuation coefficient μ of each material is known. Thus, when regions where bones, a contrast medium, water, fat, and the like exist are known, the values $c_1$ and $c_2$ can be acquired by substituting $\mu_1$ ($E_{Low}$), $\mu_2$ ($E_{Low}$), $\mu_1$ ($E_{High}$) and $\mu_2$ ($E_{High}$) at two different types of X-ray energy into Eq. (1) above and by solving a simultaneous equation given by Eq. (2) below, where the two different types of X-ray energy occur when two different types of X-ray tube voltage, i.e., High-kV (high X-ray tube voltage) and Low-kV (low X-ray tube voltage) are used. This is because there are only two unknown quantities, $c_1$ and $c_2$, in Eq. (2) below.

$$\mu(E_{Low}) = \mu_1(E_{Low})c_1 + \mu_2(E_{Low})c_2$$

$$\mu(E_{High}) = \mu_1(E_{High})c_1 + \mu_2(E_{High})c_2 \quad (2)$$

The character "E" in Eq. (2) above is X-ray energy. The subscripts "Low" and "High" are low energy and high energy at two different types of X-ray energy. The character "μ" is the linear attenuation coefficient of each material at X-ray energy E.

By determining a slope and intercept of a straight line linking $c_1$ and $c_2$ with water, it is possible to acquire a slope a and intercept b of a straight line for a mixture of each material with water. Consequently, correlations similar to those in FIG. 6 can be acquired. In this way, materials can be discriminated by comparing information provided by linear equations acquired using a method which involves radiographing a known materials beforehand or a method which involves carrying out calculations using linear attenuation coefficients with information on $c_1$ (x, y) and $c_2$ (x, y) which is based on reference material images generated by the reconstruction unit 73 from the projection data of dual energy.

Note that although in the first embodiment, reference materials are separated on the basis of pre-reconstruction data and materials are discriminated on the basis of reference material images, other measures may be taken as long as reference materials can be separated and materials can be discriminated.

The materials discrimination unit 74 supplies a discrimination result of each material existing in the radiographic coverage to the energy setting unit 75.

In step S7, the energy setting unit 75 acquires the discrimination results from the materials discrimination unit 74. The energy setting unit 75 reads out the energy table prestored in the HDD 43 or memory 42 of the image processing apparatus 12.

FIG. 7 is a diagram showing a configuration example of the energy table prestored in the HDD 43 or memory 42 of the image processing apparatus 12.

As shown in FIG. 7, materials and the energies required to generate monochromatic X-ray images for the materials are stored by being associated with each other. For example, Material A is stored by being associated with 75 [keV] as the energy required to generate a monochromatic X-ray image for Material A. Also, Bone is stored by being associated with 130 [keV] as the energy required to generate a monochromatic X-ray image for artifacts. Furthermore, Artifact is stored by being associated with 130 [keV] as the energy required to generate a monochromatic X-ray image for the artifact. Note that materials need not be composed of only an arbitrary material, and an energy may be associated with a mixture of two materials or associated with one material.

The energies stored in the energy table by being associated with materials are, so to say, appropriate energies for the materials and in determining the appropriate energies as referred to herein, various factors are taken into consideration, including, for example, ease of providing clear contrast due to large differences in CT value and capability to remove bones and artifacts.

By referring to the energy table, the energy setting unit 75 sets energy at which a monochromatic X-ray image for each material existing in the radiographic coverage will be generated. Note that as the energy is set here for each material at a high resolution, a monochromatic X-ray image can be created at a high resolution subsequently in a process of step S8.

The energy setting unit 75 supplies data on the set energy to the monochromatic X-ray image generating unit 76.

In step S8, the monochromatic X-ray image generating unit 76 generates a monochromatic X-ray image for each material existing in the radiographic coverage on the basis of the energy set by the energy setting unit 75 for each material and the two reference material images generated by the reconstruction unit 73. In so doing, the monochromatic X-ray CT image is defined by Eq. (3) below.

$$CT\ number(E, x, y) = 1000 \times \frac{\mu(E, x, y) - \mu_{water}(E, x, y)}{\mu_{water}(E, x, y)} \quad (3)$$

The member "$\mu_{water}$ (E, x, y)" in Eq. (3) above is the linear attenuation coefficient of water. The member "μ (E, x, y)" is the X-ray attenuation coefficient acquired for the material and is given by Eq. (1) above. Thus, if information on $c_1$ (x, y) and $c_2$ (x, y) is acquired for each pixel (voxel) in a process of step S6, the linear attenuation coefficient μ (E, x, y) at an arbitrary energy is found from Eq. (1) above and a monochromatic X-ray image at the arbitrary energy can be acquired by substituting the linear attenuation coefficient into Eq. (3) above. As a result of this calculation, after the material discrimination described above, a monochromatic X-ray image is generated for each material at the arbitrary energy.

The monochromatic X-ray image generating unit 76 supplies data on the generated monochromatic X-ray image to the fusion image generating unit 77. Note that the monochromatic X-ray image generating unit 76 may generate a monochromatic X-ray image for each material at an arbitrary energy that a user specifies via a user input device 44.

In step S9, the fusion image generating unit 77 generates a fusion (combined) image based on the monochromatic X-ray images generated by the monochromatic X-ray image generating unit 76. Specifically, as shown in FIG. 8, the fusion image generating unit 77 fuses (superimposes or combines) the monochromatic X-ray images for respective materials and generates a fusion image (combined image).

Figure 8:
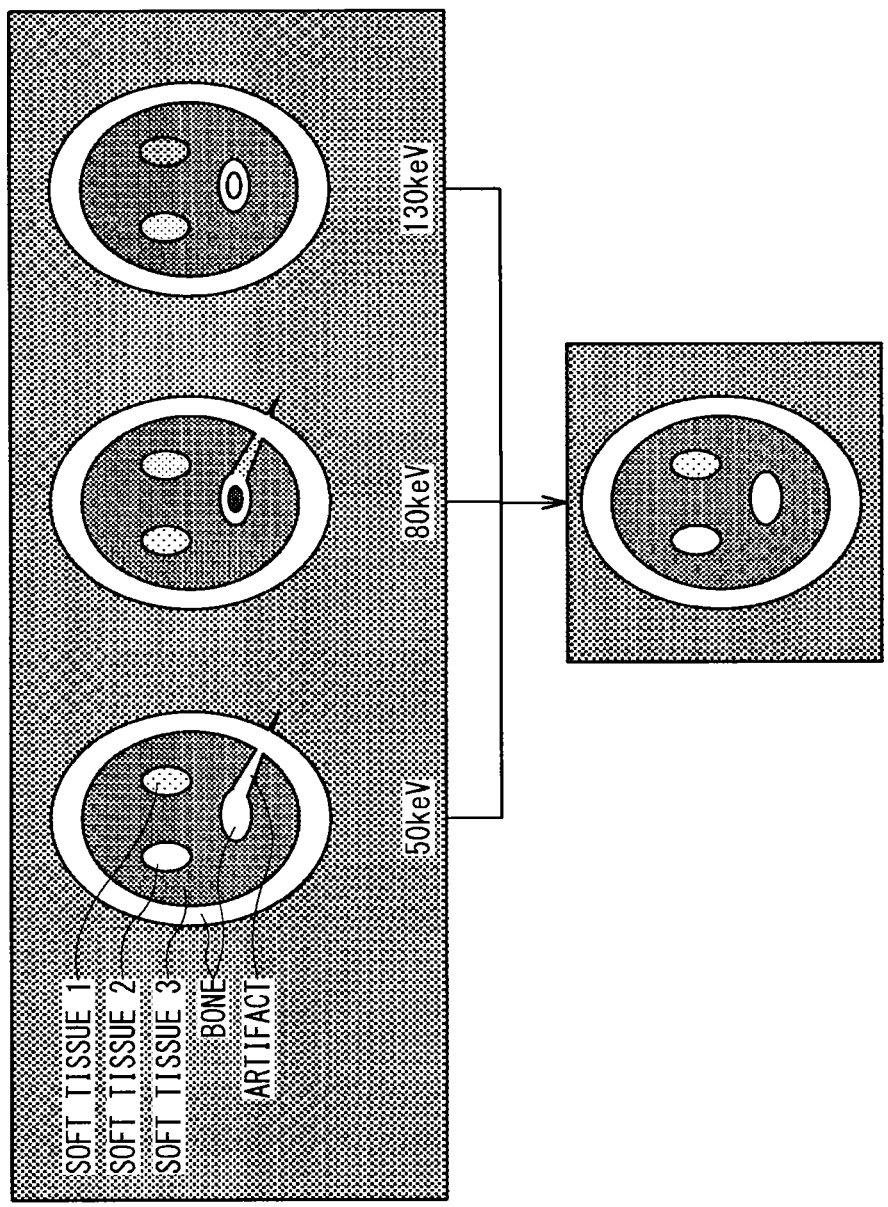
FIG. 8 is a diagram for illustrating a concept of generating a fusion image.

FIGS. 8 and 9 are diagrams for illustrating a concept of generating a fusion image.

As shown in FIG. 9, it is assumed that the energy (optimum energy) set for Soft Tissue 1 is 80 [keV], that the energy (optimum energy) set for Soft Tissue 2 is 50 [keV], and that the energy (optimum energy) set for Soft Tissue 3 is 50 [keV]. Also, it is assumed that the energy set for Bone is 130 [keV] and that the energy set for Artifact is 130 [keV]. In this case, as shown in FIG. 8, a monochromatic X-ray image is generated (created) for Soft Tissue 1 at an energy of 80 [keV], and monochromatic X-ray images are generated for Soft Tissues 2 and 3 at an energy of 50 [keV], and monochromatic X-ray images are generated for Bone and Artifact at an energy of 130 [keV]. Then, the three monochromatic X-ray images generated for Soft Tissue's 1 to 3, Bone, and Artifact are fused (combined) to generate a fusion image.

Note that the fusion image generating unit 77 may apply a weighted addition process or weighted subtraction process to specific images among the monochromatic X-ray images for respective materials using desired coefficients. This will make it possible to highlight a specific monochromatic X-ray image instead of integrating the monochromatic X-ray images for respective materials uniformly in equal proportions.

The fusion image generating unit 77 supplies the generated fusion image to the display device 45. In step S10, the CPU 41 controls the display device 45 so as to display the generated fusion image. Any of 2D display (two-dimensional display) and 3D display (three-dimensional display) may be used for the fusion image. Note that the CPU 41 may display each monochromatic X-ray image as it is on the display device 45 rather than integrating the monochromatic X-ray images for respective materials. In so doing, the CPU 41 may display each monochromatic X-ray image in colors on the display device 45 using different colors or display the monochromatic X-ray image in 2D display mode or 3D display (three-dimensional display) mode. Also, a single monochromatic X-ray image may be multiplied by weighting coefficients to display a weighted image or suppressed image.

Note that since the energy required to generate a monochromatic X-ray image varies from material to material, it is conceivable that the CT values displayed on the display device 45 may vary as well. Thus, the energy may be varied among materials only for image display as described above, by fixing the CT values displayed on the display device 45 at a specific energy.

Also, when performing the fusion image display process, the X-ray CT apparatus 1 according to the first embodiment generates projection data by performing dual energy scanning or multi-energy scanning. However, the present invention is applicable not only to such cases, but also to when projection data generated by dual energy scanning or multi-energy scanning performed beforehand is stored in the HDD 43.

The X-ray CT apparatus 1 according to the first embodiment can create an image at an arbitrary energy for each material based on pre-reconstruction data of multi-energy and then create and display a singe fusion image. Consequently, the X-ray CT apparatus 1 according to the first embodiment eliminates the need to select one of conceivable candidate energies even if optimum energy for diagnostic imaging varies with a subject's diagnosis region, materials, and the like. Also, the X-ray CT apparatus 1 according to the first embodiment can provide images with reduced artifacts and with contrast improved on a material by material basis even if the optimum energy for diagnostic imaging varies with a subject's diagnosis region, materials, and the like.

(Variation)

The X-ray CT apparatus 1 according to the first embodiment described above is configured to perform dual energy scanning to obtain projection data of multi-energy. A variation of the X-ray CT apparatus 1 is designed to obtain projection data of multi-energy by performing a single energy scan in a "multilayer system" which uses X-ray detectors of a multilayered structure.

According to the variation of the X-ray CT apparatus 1 the X-ray detector 23 (illustrated in FIG. 1) has a multilayered structure, for example, a two-layer structure (a detector in a shallow layer and a detector in a deep layer). In that case, low-energy X-rays are detected by the detector in the shallow layer and high-energy X-rays passing through the shallow layer is detected by the detector in the deep layer. The projection data reading unit 71 (illustrated in FIG. 4) reads the projection data of dual energy out of the HDD 43 of the image processing apparatus 12, the dual energy being obtained from each layer of the two-layer structure. Note that the operation of the separation unit 72 (illustrated in FIG. 4) and subsequent components of the X-ray CT apparatus 1 are also applicable to the variation of the X-ray CT apparatus 1.

Second Embodiment

An X-ray CT apparatus according to a second embodiment is a photon counting X-ray CT apparatus.

Figure 10:
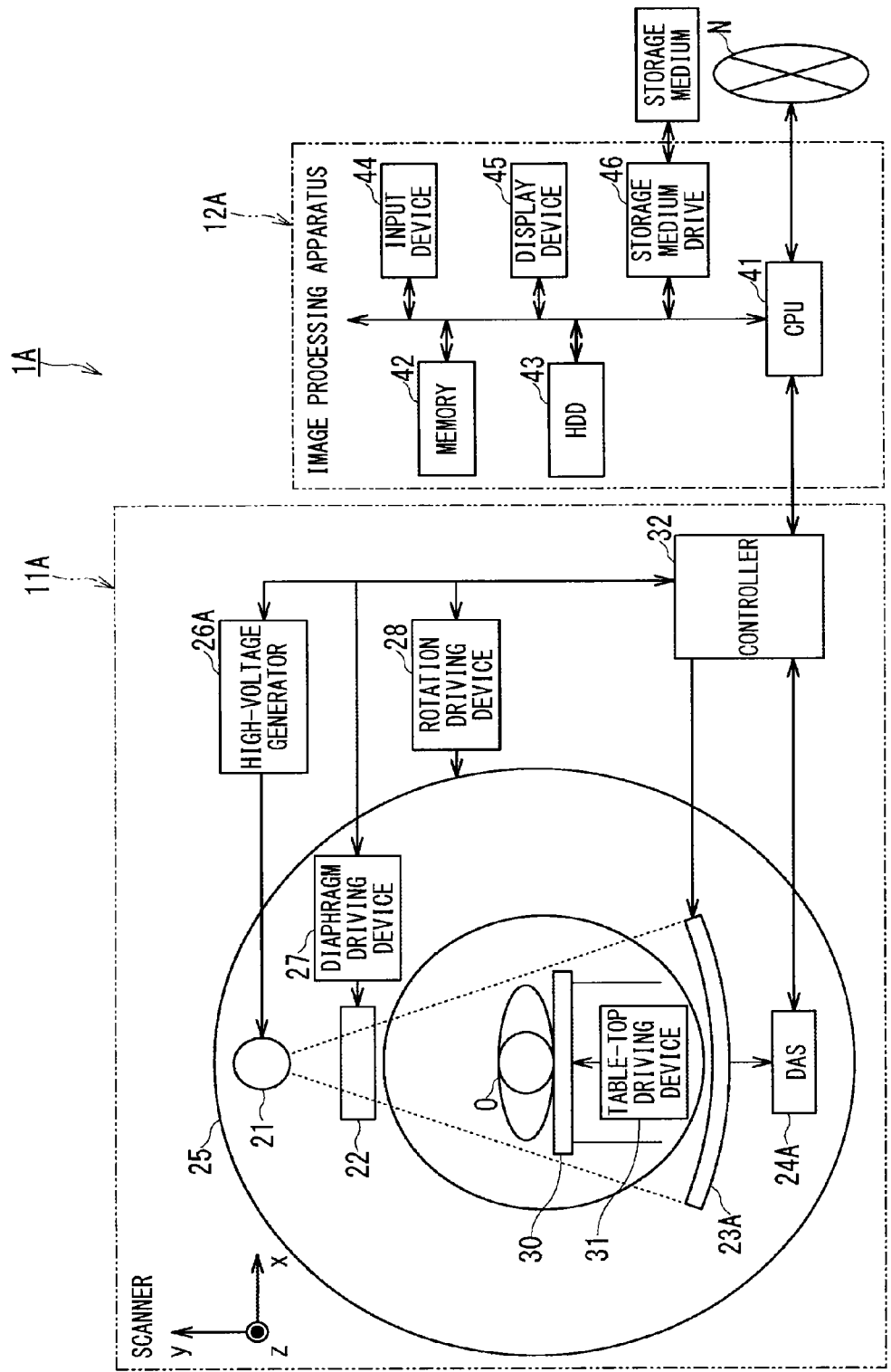
FIG. 10 is a diagram showing a configuration example of an X-ray CT apparatus according to a second embodiment.

FIG. 10 is a diagram showing a configuration example of the X-ray CT apparatus according to the second embodiment.

FIG. 10 shows the X-ray CT apparatus 1A according to the second embodiment. The X-ray CT apparatus 1A is mainly made up of a scanner 11A and an image processing apparatus (console) 12A. The scanner 11A of the X-ray CT apparatus 1A is normally installed in an examination room and used to generate X-ray transmission data on a patient O (subject). On the other hand, the image processing apparatus 12A is normally installed in a control room next to the examination room and used to generate projection data based on the transmission data and generate and display a reconstructed image.

The scanner 11A of the X-ray CT apparatus 1A includes an X-ray tube 21, an diaphragm 22, an X-ray detector (photon counting image detector) 23A, a DAS 24A, a rotary unit 25, a high-voltage generator 26A, an diaphragm driving device 27, a rotation driving device 28, a table-top 30, a table-top driving device 31, and a controller 32.

In the configuration of the X-ray CT apparatus 1A shown in FIG. 10, the same components as those in the X-ray CT apparatus 1 shown in FIG. 1 are denoted by the same reference numerals as the corresponding components in FIG. 1, and description thereof will be omitted.

The X-ray detector 23A is arranged in a matrix with plural channels in a channel direction and plural columns of pixels in a slice direction. Moreover, the X-ray detector 23A is curved in the channel direction, especially by considering a divergence angle of an X-ray beam from the X-ray tube 21. Note that an overall shape of the X-ray detector 23A depends on its application, and may be planar. A semiconductor detector will be described below as an example, but the present invention is applicable not only to semiconductor detectors, but also to any type of detector capable of photon calculation.

Figure 11:
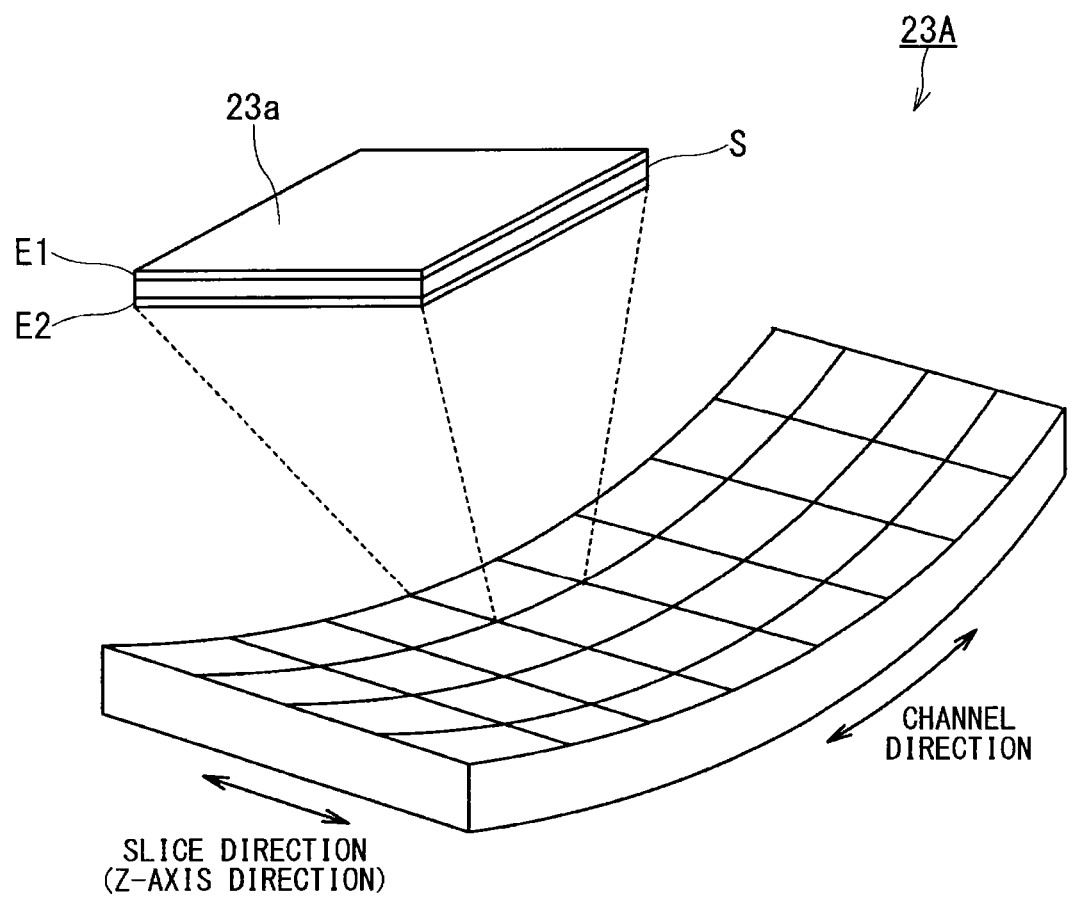
FIG. 11 is a diagrammatic perspective view for illustrating a configuration of an X-ray detector of the X-ray CT apparatus according to the second embodiment.

FIG. 11 is a diagrammatic perspective view for illustrating a configuration of the X-ray detector 23A of the X-ray CT apparatus 1A according to the second embodiment.

As shown in FIG. 11, dividing a two-dimensional plane into plural planes, the X-ray detector 23A is divided into plural detector blocks 23a, which are able to be detachably coupled. Also, a radiolucent image from the X-ray tube 21 is designed to be obtained by a collimator (not shown) placed in front of the detector blocks 23a on the X-ray incidence side, the collimator being made of molybdenum or tungsten.

Each detector block 23a is constructed from a compound semiconductor and provided with a monolithic structure made up of a layered semiconductor cell S of a predetermined size (e.g., a few centimeters by a few centimeters), an electrically charged electrode E1 for voltage application, and plural collecting electrodes E2 arranged in a two-dimensional array (on a grid), where the electrically charged electrode E1 covers a radiation incidence surface of the semiconductor cell S while the collecting electrodes E2 divide and cover a surface of the semiconductor cell S opposite the radiation incidence surface. The collecting electrodes E2 correspond to individual pixels. Materials available for the semiconductor cell S include a cadmium telluride semiconductor (CdTe semiconductor), cadmium zinc telluride semiconductor (CdZnTe semiconductor), and silicon semiconductor (Si semiconductor). A relatively high voltage on the order of, for example, a few tens of volts to a few hundred volts is applied to the electrically charged electrode E1. Consequently, pairs of an electron and positive hole are produced in the semiconductor cell S by X-ray photons incident on the semiconductor cell S, the electrons are collected by the collecting electrodes E2, which are positive with respect to the electrons, and an electric charge of the electrons is detected as a pulsed signal. That is, the X-rays incident on the radiation incidence surface is directly converted into a pulsed signal of a quantity of electricity.

A size of each pixel with respect to X-rays depends on a size of each of the plural collecting electrodes E2 resulting from division into a grid. The size is small enough to allow X-rays to be detected as photons (particles). As a result, the X-ray detector 23A is configured to be able to count photons and a predetermined number of pixel channels are formed in a matrix on the entire X-ray detector 23A.

Consequently, the X-rays transmitted through the patient O are counted as X-ray particles (i.e., X-ray photons) by the X-ray detector 23A at fixed time intervals and a detection signal of an analog amount corresponding to photon energy is outputted from each pixel P (each of pixels P1 to Pk).

The detection signal of each pixel outputted from the X-ray detector 23A is sent to the DAS 24A.

Figure 12:
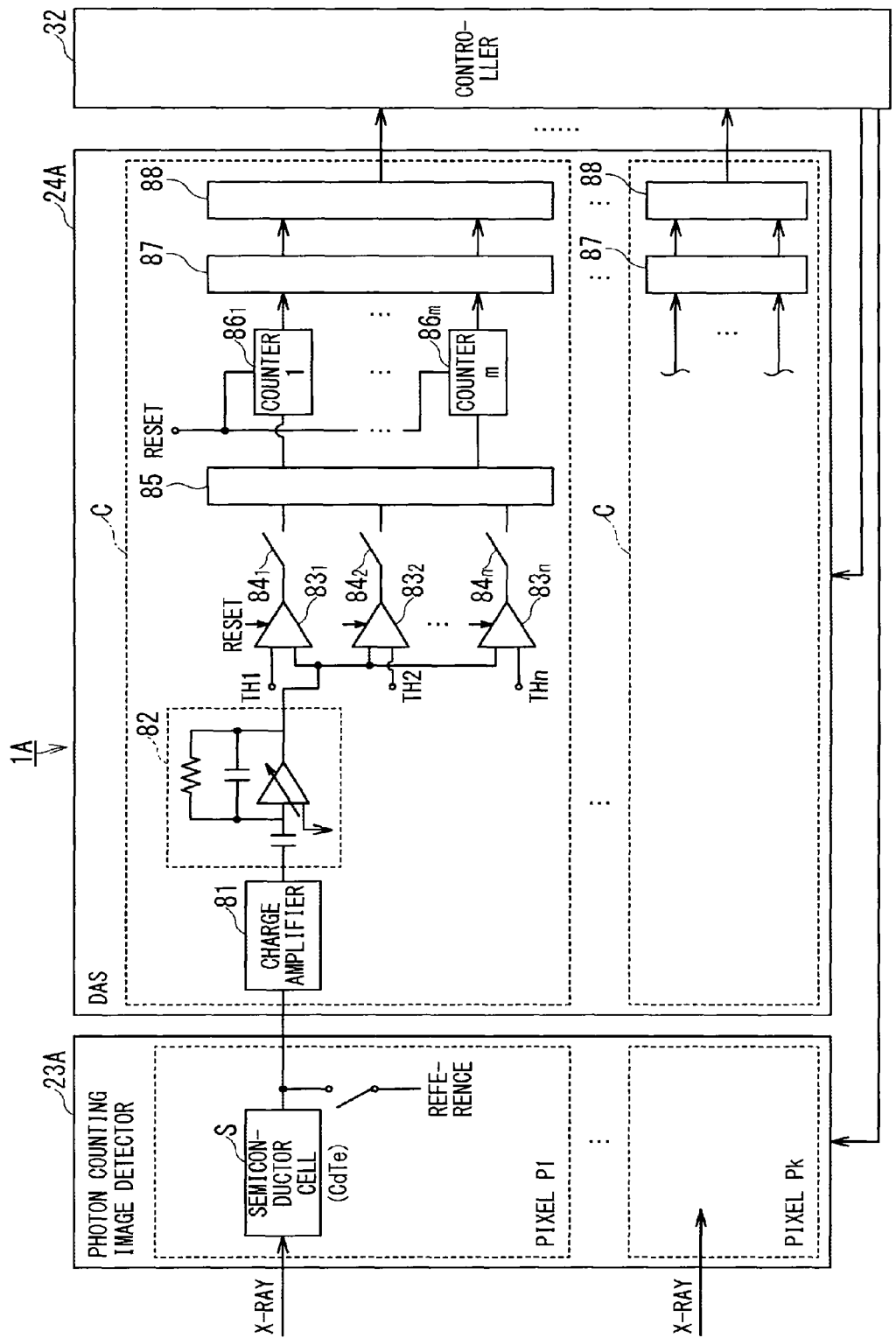
FIG. 12 is an electrical block diagram around the X-ray detector and a DAS in the X-ray CT apparatus according to the second embodiment.

FIG. 12 is an electrical block diagram around the X-ray detector 23A and DAS 24A in the X-ray CT apparatus 1A according to the second embodiment.

As shown in FIG. 12, each pixel P of the X-ray detector 23A includes a semiconductor cell S, which is controlled by the controller 32.

The DAS 24A includes a processing circuit C for each pixel P, where the processing circuit C is controlled by the controller 32. The processing circuit C includes a charge amplifier 81, a waveform shaping circuit 82, comparators (Dual Discri) $83_1$ to $83_n$ of first to nth stages (n is a positive integer), switches $84_1$ to $84_n$ of first to nth stages, a threshold logic circuit (Discri Logic) 85, counters (CLK) $86_1$ to $86_m$ of first to mth stages, a weighting circuit 87, and an adder circuit 88.

The charge amplifier 81 is connected to each of the plural collecting electrodes E2 of the semiconductor cell S. The charge amplifier 81 outputs an electric charge collected in response to incidence of X-ray particles, as a voltage pulse signal. An output end of the charge amplifier 81 is connected to the waveform shaping circuit 82 whose gain and offset are adjustable.

The waveform shaping circuit 82 shapes a waveform of a detected voltage pulse signal by processing the waveform at a preset gain and offset. The gain and offset of the waveform shaping circuit 82 are adjustable parameters which allow for nonuniformity of charging characteristics among pixels of the semiconductor cell S. By adjusting the gain and offset of the waveform shaping circuit 82 of each pixel via a calibration operation in advance, it is possible to perform waveform shaping by eliminating the nonuniformity described above. Consequently, the pulse signal outputted from the waveform shaping circuit 82 of each acquisition channel after waveform shaping has characteristics which substantially reflect an energy amount of incident X-ray particles, almost dissolving dispersion among the pixels. An output end of the waveform shaping circuit 82 is connected to a comparison input end of each of the plural comparators $83_1$ to $83_n$.

Reference values TH1 (upper limit reference value THH) to THn (lower limit reference value THL) differing from one another are applied to respective input ends of the comparators $83_1$ to $83_n$. By comparing a peak value (energy of an absorbed X-ray photon) of one pulse signal from the waveform shaping circuit 82 with different reference values TH1 to THn, it is possible to separate the energy of the X-ray photon (X-ray particle) absorbed by the semiconductor cell S into one of plural energy regions set in advance. For example, when n is 3, the energy region into which the X-ray photon energy is separated varies depending on which of the reference values TH1 to TH3 the peak value of the pulse signal exceeds. When the peak value is between the reference values TH1 to TH2, the energy of the absorbed X-ray photon is separated so as to be included in a first energy region. When the peak value is between the reference values TH2 to TH3, the energy of the absorbed X-ray photon is separated so as to be included in a second energy region. When the peak value is equal to or smaller than the reference value TH3 (lower limit reference value THL) or equal to or larger than the reference value TH1 (upper limit reference value THH), the X-ray photon energy is separated as not causing disturbance or white noise from semiconductor cell S and charge amplifier 81 to be detected. The peak value can also become equal to or larger than the reference value TH1 (upper limit reference value THH) when two or more X-ray photons are incident on the pixel, but such an event is treated similarly to disturbance and the like as not being a major signal in forming image information because of a low probability of occurrence.

Note that the number of reference values, i.e., the number of separable energy regions is not limited to 3. The number of reference values may be 2, 4, or the like as well.

The switches $84_1$ to $84_n$ are designed to turn on when the pulse signals outputted from the respective comparators $83_n$ to $83_n$ exceed the reference values TH1 to THn of the switches $84_1$ to $84_n$ and turn off otherwise. For example, the switch $84_1$ turns on when the pulse signal outputted from the comparator $83_1$ exceeds the reference value TH1 of the switch $84_1$, and turns off otherwise. Output ends of the switches $84_1$ to $84_n$ are connected to the threshold logic circuit 85.

On the basis of the respective pulse signals outputted from the switches $84_1$ to $84_n$, the threshold logic circuit 85 senses which of the comparators $83_1$ to $83_n$ is on (off) and generates a clock pulse so as to count output pulses corresponding to a maximum pulse signal of the activated comparators $83_1$ to $83_n$. Plural output ends of the threshold logic circuit 85 are connected to respective ones of plural counters $86_1$ to $86_m$ to count clock pulses. The plural counters $86_1$ to $86_m$ act to count the pulses of pulse signals with wave heights appropriate for the respective counters. For example, pulses larger than TH2 and smaller than TH1 are counted by the counter $86_1$ and pulses larger than TH3 and smaller than TH2 are counted by the counter $86_2$ (and so on). In this case, the number m of necessary counters is m=n−1, where n is the number of comparators.

In another example, the number m of counters may be m<n−1, where n is the number of comparators. This is the case when the number of pulses is counted together in plural wave height ranges instead of counting the number of pulses separated according to wave height in each wave height range. The smallest number m of counters is m=1. In this case, since the clock pulses outputted by the threshold logic circuit 85 are counted by a single counter, the number of photons is counted without distinguishing energies of the X-ray photons.

The counters $86_1$ to $86_m$ count the numbers of X-ray photons entering the respective energy regions for a fixed period of time by counting up the clock pulses outputted from the threshold logic circuit 85.

The weighting circuit 87 assign weights to counts outputted from the respective counters $86_1$ to $86_m$.

The adder circuit 88 adds together the weighted counts classified by the energy region and outputted from the weighting circuit 87, thereby generates raw data of each pixel P, and sends the raw data to the image processing apparatus 12A via the controller 32. The adder circuit 88 generates raw data of dual energy based on plural counts from the respective energy regions as well as raw data of dual energy based on plural additional values obtained, respectively, by plural different, types of weighting.

In this way, in a set period of time before being reset, the DAS 24 counts the number of X-ray photons incident on each pixel P of the X-ray detector 23A in each of the energy regions corresponding to m counter stages using the plural counters $86_1$ to $86_m$. The counts thus obtained, i.e., the counts of the X-ray photons are read out of the plural counters $86_1$ to $86_m$ as detection data (raw data) of digital quantities. Data is read from each pixel P in an ASIC layer.

Returning to the description of FIG. 10, the high-voltage generator 26A supplies electric power necessary for X-ray irradiation to the X-ray tube 21 under the control of the controller 32.

The image processing apparatus 12A of the X-ray CT apparatus 1A is configured based on a computer and is capable of intercommunicating with a network N. As with the image processing apparatus 12 (illustrated in FIG. 1), the image processing apparatus 12a is made up of basic hardware, including a CPU 41, a memory 42, an HDD 43, an input device 44, and a display device 45. The CPU 41 is interconnected with each hardware component of the image processing apparatus 12A via a bus serving as a common signal transmission path. Note that the image processing apparatus 12A may sometimes be equipped with a storage media drive 46.

As with the image processing apparatus 12 (illustrated in FIG. 1), the image processing apparatus 12A applies a logarithmic conversion process or a correction process (pre-processing) such as sensitivity correction to raw data of dual energy received from the DAS 24A of the scanner 11A, thereby generates projection data, and stores the projection data in a storage device such as the HDD 43. Also, as with the image processing apparatus 12 (illustrated in FIG. 1), the image processing apparatus 12A removes scattered radiation from the pre-processed projection data. As with the image processing apparatus 12 (illustrated in FIG. 1), the image processing apparatus 12A removes the scattered radiation on the basis of values of the projection data in an X-ray exposure range, and makes scattered radiation correction by subtracting the scattered radiation estimated from magnitude of value of projection data to be subjected to scattered radiation correction or adjacent projection data from the projection data to be corrected. As with the image processing apparatus 12 (illustrated in FIG. 1), the image processing apparatus 12A generates image data based on the corrected projection data and stores the image data in a storage device such as the HDD 43 or displays the image data on the display device 45.

Figure 13:
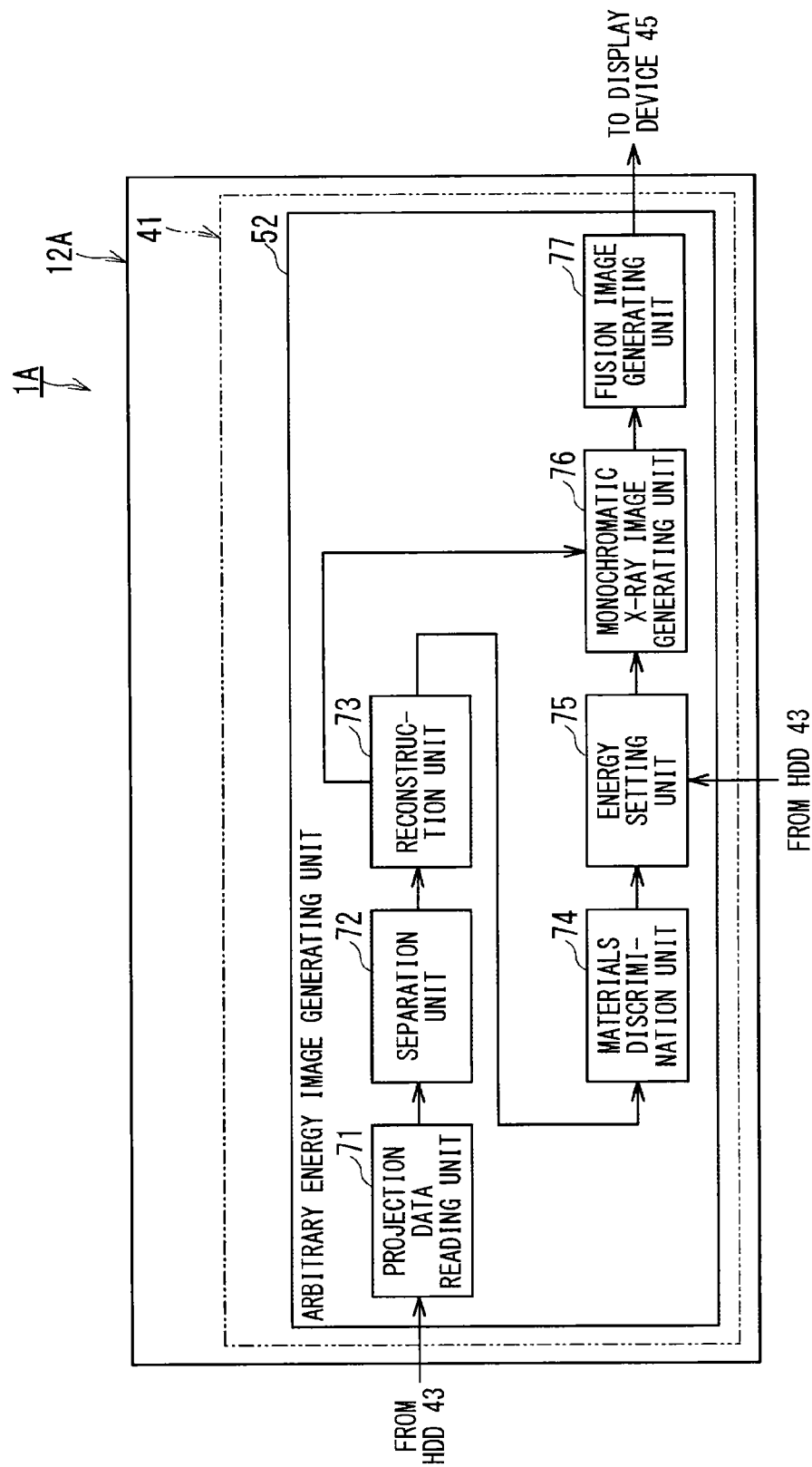
FIG. 13 is a block diagram showing functions of the X-ray CT apparatus according to the second embodiment.

FIG. 13 is a block diagram showing functions of the X-ray CT apparatus 1A according to the second embodiment.

As the CPU 41 of the image processing apparatus 12A shown in FIG. 10 executes a program, the X-ray CT apparatus 1A functions as an arbitrary energy image generating unit 52 as shown in FIG. 13. Specifically, the arbitrary energy image generating unit 52 includes a projection data reading unit 71, a separation unit 72, a reconstruction unit 73, a materials discrimination unit 74, an energy setting unit 75, a monochromatic X-ray image generating unit 76, and a fusion image generating unit 77. Note that all or part of the arbitrary energy image generating unit 52 of the image processing apparatus 12A may be provided as hardware on the image processing apparatus 12. Also, all or part of the arbitrary energy image generating unit 52 of the image processing apparatus 12A may be provided not only on the image processing apparatus 12A, but also on the high-voltage generator 26A and controller 32.

In functions of the X-ray CT apparatus 1A shown in FIG. 13, the same components as those in the X-ray CT apparatus 1 shown in FIG. 1 are denoted by the same reference numerals as the corresponding components in FIG. 1, and description thereof will be omitted.

Figure 14:
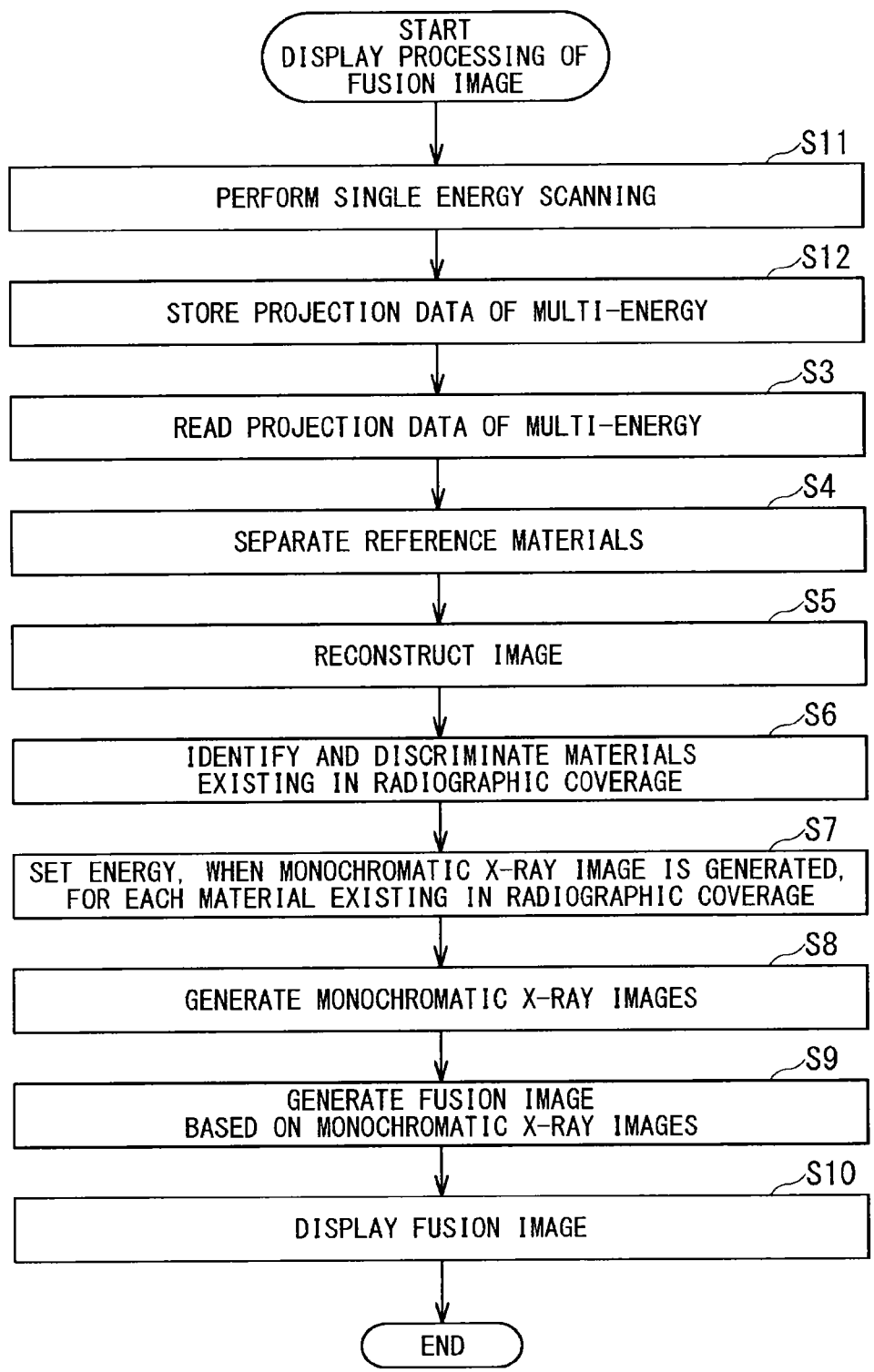
FIG. 14 is a flowchart showing an operation of the X-ray CT apparatus according to the second embodiment.

FIG. 14 is a flowchart showing an operation of the X-ray CT apparatus 1A according to the second embodiment.

In the operation of the X-ray CT apparatus 1A shown in FIG. 14, the same steps as those in the X-ray CT apparatus 1 shown in FIG. 5 are denoted by the same step numbers as the corresponding steps in FIG. 5, and description thereof will be omitted.

In step S11, the scanner 11A of the X-ray CT apparatus 1A performs single energy scanning under the control of the controller 32.

In step S12, the DAS 24A of the scanner 11A generates raw data of dual energy based on plural counts from the respective energy regions as well as raw data of dual energy based on plural additional values obtained, respectively, by plural different types of weighting. Output data of the DAS 24A is supplied to the image processing apparatus 12A via the controller 32 of the scanner 11A.

Then, the CPU 41 of the image processing apparatus 12A of the X-ray CT apparatus 1A acquires raw data of dual energy inputted by the DAS 24A of the scanner 11A, applies a logarithmic conversion process or a correction process (pre-processing) such as sensitivity correction to the acquired raw data, thereby generates projection data of dual energy, and stores the projection data in a storage device such as the HDD 43. Under the control of the CPU 41, the HDD 43 stores projection data of dual energy.

Also, when performing the fusion image display process, the X-ray CT apparatus 1A according to the second embodiment generates projection data by performing single energy scanning. However, the present invention is applicable not only to such cases, but also to when projection data generated by single energy scanning performed beforehand is stored in the HDD 43.

The X-ray CT apparatus 1A according to the second embodiment can create an image at an arbitrary energy for each material on the basis of pre-reconstruction data of dual energy and then create and display a single fusion image. Consequently, the X-ray CT apparatus 1A according to the second embodiment eliminates the need to select one of conceivable candidate energies even if optimum energy for diagnostic imaging varies with a subject's diagnosis region, materials, and the like. Also, the X-ray CT apparatus 1A according to the second embodiment can provide images with reduced artifacts and with contrast improved on a material by material basis even if the optimum energy for diagnostic imaging varies with a subject's diagnosis region, materials, and the like.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   an X-ray tube configured to emit X-rays;
   a high-voltage power supply configured to apply an X-ray tube voltage to the X-ray tube;
   an X-ray detector equipped with X-ray detecting elements and configured to detect the X-rays;
   an image generating unit configured to generate multiple reference material images corresponding to respective ones of multiple reference materials on a basis of pre-reconstruction data of multi-energy obtained by scanning a subject;
   a discrimination unit configured to discriminate each of multiple materials contained in an imaging region of the subject on a basis of the multiple reference material images;
   an energy level setting unit configured to set multiple energy levels of the corresponding multiple materials;
   a monochromatic X-ray image generating unit configured to generate multiple monochromatic X-ray images corresponding to the multiple energy levels, the multiple monochromatic X-ray images each being based on the multiple reference material images;
   a combined-image generating unit configured to combine the multiple monochromatic X-ray images corresponding to the multiple materials and to generate a combined image; and
   a display unit configured to display the combined image on a display device.

2. The X-ray CT apparatus according to claim 1, wherein the image generating unit obtains the pre-reconstruction data of multi-energy by scanning the subject, which is one of dual energy scanning and multi-energy scanning performed using multiple different X-ray tube voltages.

3. The X-ray CT apparatus according to claim 2, wherein the discrimination unit expresses an X-ray attenuation coefficient acquired for each of the materials as a sum of products obtained by multiplying multiple X-ray attenuation coefficients of the multiple reference materials by respective predetermined coefficients on a basis of the multiple reference material images obtained during the dual energy scanning or the multi-energy scanning, and determines a material contained in the imaging region of the subject on a basis of a correlation among the predetermined coefficients.

4. The X-ray CT apparatus according to claim 1, wherein:
   the X-ray detector is a photon counting image detector; and
   the image generating unit obtains the pre-reconstruction data of multi-energy on a basis of multiple counts corresponding to respective ones of the multiple energy regions.

5. The X-ray CT apparatus according to claim 1, wherein:
   the X-ray detector is an X-ray detector of a multilayered structure; and
   the image generating unit obtains the pre-reconstruction data of multi-energy from each layer of the multilayered structure.

6. The X-ray CT apparatus according to claim 1, wherein the combined-image generating unit generates the combined image by applying one of a weighted addition process and a weighted subtraction process to the multiple monochromatic X-ray images.

7. The X-ray CT apparatus according to claim 1, wherein the display unit displays a monochromatic X-ray image corresponding to each of the materials.

8. The X-ray CT apparatus according to claim 1, wherein the display unit displays a monochromatic X-ray image corresponding to each of the materials in colors.

9. The X-ray CT apparatus according to claim 1, wherein the display unit displays a monochromatic X-ray image subjected to one of a weighted addition process and a weighted subtraction process.

10. The X-ray CT apparatus according to claim 1, wherein the display unit displays the combined-image two-dimensionally or three-dimensionally.

11. The X-ray CT apparatus according to claim 1, wherein the display unit displays the combined-image, but displays CT values only at a specific energy level by fixing CT value display at the specific energy level when displaying CT values in the imaging region of the subject.

12. The X-ray CT apparatus according to claim 1, wherein the monochromatic X-ray image generating unit generates a monochromatic X-ray image at an arbitrary energy level for each of the multiple materials.

13. The X-ray CT apparatus according to claim 1, further comprising,
   a storage unit configured to store each of the multiple materials in a table by associating the multiple materials with the corresponding energy levels at which the multiple monochromatic X-ray images are generated by the monochromatic X-ray image generating unit, wherein
   the monochromatic X-ray image generating unit generates the monochromatic X-ray image by referring to the table stored in the storage unit and setting the energy level determined by each of the materials.

14. An image processing apparatus comprising:
   an image generating unit configured to generate multiple reference material images corresponding to respective ones of multiple reference materials on a basis of pre-reconstruction data of multi-energy obtained by scanning a subject;
   a discrimination unit configured to discriminate each of multiple materials contained in an imaging region of the subject on a basis of the multiple reference material images;
   an energy level setting unit configured to set multiple energy levels of the corresponding multiple materials;
   a monochromatic X-ray image generating unit configured to generate multiple monochromatic X-ray images corresponding to the multiple energy levels, the multiple monochromatic X-ray images each being based on the multiple reference material images;

a combined-image generating unit configured to combine the multiple monochromatic X-ray images corresponding to the multiple materials and to generate a combined image; and a display unit configured to display the combined image on a display device.

15. An image processing method comprising:

generating multiple reference material images corresponding to respective ones of multiple reference materials on a basis of pre-reconstruction data of multi-energy, stored in a storage, obtained by scanning a subject;

discriminating each of multiple materials contained in an imaging region of the subject on a basis of the multiple reference material images;

setting multiple energy levels of the corresponding multiple materials;

generating multiple monochromatic X-ray images corresponding to the multiple energy levels, the multiple monochromatic X-ray images each being based on the multiple reference material images;

combining the multiple monochromatic X-ray images corresponding to the multiple materials and generating a combined image; and displaying the combined image on a display device.

* * * * *